(12) United States Patent
Davis et al.

(10) Patent No.: US 7,375,096 B1
(45) Date of Patent: *May 20, 2008

(54) METHOD OF PREPARING A SUPRAMOLECULAR COMPLEX CONTAINING A THERAPEUTIC AGENT AND A MULTI-DIMENSIONAL POLYMER NETWORK

(75) Inventors: Mark E. Davis, Pasadena, CA (US); Hector Gonzalez, San Francisco, CA (US); Suzie (Sue Jean) Hwang, Torrance, CA (US)

(73) Assignee: California Institute of Technology, Pasadena, CA (US)

( * ) Notice: Subject to any disclaimer, the term of this patent is extended or adjusted under 35 U.S.C. 154(b) by 713 days.

This patent is subject to a terminal disclaimer.

(21) Appl. No.: 09/453,707

(22) Filed: Dec. 3, 1999

Related U.S. Application Data

(60) Provisional application No. 60/127,856, filed on Apr. 5, 1999, provisional application No. 60/110,847, filed on Dec. 4, 1998.

(51) Int. Cl.
*A61K 31/724* (2006.01)
*A61K 8/11* (2006.01)
*C12N 15/63* (2006.01)

(52) U.S. Cl. .................... 514/58; 424/486; 424/488; 435/455; 527/300

(58) Field of Classification Search .............. 536/103, 536/105, 106, 124; 514/58
See application file for complete search history.

(56) References Cited

U.S. PATENT DOCUMENTS

| | | | | |
|---|---|---|---|---|
| 4,582,865 | A | * | 4/1986 | Balazs et al. .................. 524/29 |
| RE32,268 | E | * | 10/1986 | Gordon .......................... 514/25 |
| 4,727,064 | A | | 2/1988 | Pitha ............................. 514/58 |
| 4,774,329 | A | | 9/1988 | Friedman ..................... 536/103 |
| 4,818,542 | A | * | 4/1989 | DeLuca et al. .............. 424/491 |
| 5,276,088 | A | | 1/1994 | Yoshinaga .................. 525/54.3 |
| 5,608,015 | A | | 3/1997 | Yoshinaga .................... 526/75 |
| 5,652,347 | A | * | 7/1997 | Pouyani et al. ............. 536/18.5 |
| 5,656,611 | A | * | 8/1997 | Kabanov et al. ............... 514/44 |
| 5,691,316 | A | | 11/1997 | Agrawal et al. ............... 514/44 |
| 5,693,768 | A | * | 12/1997 | Bachmann et al. ........... 536/4.1 |
| 5,700,848 | A | * | 12/1997 | Soon-Shiong et al. ......... 522/7 |
| 5,855,900 | A | | 1/1999 | Nobuhiko .................... 424/425 |
| 5,880,154 | A | | 3/1999 | Boukrinskaia et al. ...... 514/561 |
| 6,048,736 | A | | 4/2000 | Kosak .......................... 436/536 |
| 6,132,734 | A | * | 10/2000 | Thomas et al. ............. 424/275.1 |
| 6,207,195 | B1 | * | 3/2001 | Walsh et al. ................. 424/489 |
| 6,353,055 | B1 | * | 3/2002 | Kabanov et al. ........... 535/92 A |
| 6,420,176 | B1 | * | 7/2002 | Liszewicz et al. ......... 435/455 |
| 6,509,323 | B1 | * | 1/2003 | Davis et al. .................. 514/58 |
| 6,737,447 | B1 | | 5/2004 | Smith et al. |
| 2001/0034333 | A1 | | 10/2001 | Kosak ........................... 514/44 |
| 2001/0044412 | A1 | | 11/2001 | Wolff et al. .................... 514/44 |

FOREIGN PATENT DOCUMENTS

| | | |
|---|---|---|
| EP | 0 730 869 | 9/1996 |
| FR | 2 665 169 | 1/1992 |
| GB | 1 390 479 | 4/1975 |
| GB | 2197720 * | 5/1988 |
| WO | 94/02518 | 2/1994 |
| WO | WO 96/09073 A1 | 3/1996 |
| WO | 00/01734 | 1/2000 |
| WO | WO 00/33885 | 6/2000 |
| WO | WO 00/40962 | 7/2000 |
| WO | WO 00/75162 | 12/2000 |
| WO | WO 00/75164 | 12/2000 |
| WO | WO 01/37665 | 5/2001 |
| WO | WO 02/057424 | 7/2002 |

OTHER PUBLICATIONS

*Pierce 1989 Handbook and General Catalog,* Rockford, Illinois, 1989, only pp. 288-293 supplied.*
Tabushi et al., "Artificial Receptor Recognizing Hydrophobic Carbonyl Compounds," *J. Organic Chemistry,* 51(10), 1918-1921 (Mar. 16, 1986).*
U.S. Appl. No. 09/067,921, filed Apr. 29, 1998, Kosar et al.*
Alyaudrin et al., "PEG-cyclodextrin for Tranport of Neurotropic Drug to Brain," Russian Patent No. 2 094 059 C1, Oct. 27, 1997; See also *Izobreteniya,* 1997(30), 167; *Chemical Abstracts,* 129(13), p. 1016, Abstract No. 166200x (Sep. 29, 1998); see also HCAPlus Abstract, 1998, citation 520345; only abstract and first page of HCAPlus citation supplied.*
Alexakis, T. et al. "Microencapsulation of DNA within Alginate . . . " Appl. Biochem. Biotechnol. (1995) vol. 50, pp. 93-106.*
Pulfer, S. et al. "Incorporation of nitric oxide-releasing crosslinked polyethyleneimine . . . " J. Biomed. Mat. Res. (1997) vol. 37, No. 2, pp. 182-189.*
Tanaka, R. et al "High molecular weight poly(ethylenimine) . . . " Macromolecules (1983) vol. 16, No. 6, pp. 849-853.*
Ferrari, S. et al "ExGen 500 is an efficient vector for gene delivery . . . " Gene Therapy (1997) vol. 4, pp. 1100-1106.*
Trubetskoy, Vladimir S. et al., "Self-Assembly of DNA-Polymer Complexes Using Template Polymerization", *Nucleic Acids Research,* 26, No. 18, pp. 4178-4185 (1998).
Zanta, Maria-Antoniette et al., "In Vitro Gene Delivery to Hepatocytes with Galactosylated Polyethylenimine", *Bioconjugate Chem.,* 8, pp. 839-844 (1997).
Husain, Noni et al., "Complexation of Doxorubicin with β- and γ-Cyclodextrins", *Applied Spectroscopy,* 46, No. 4, pp. 652-658 (1992).
Tabushi, Iwao et al., "Specification Bifunctionalization on Cyclodextrin", *Tetrahedron Letters,* No. 18, pp. 1527-1530 (1977).
Tabushi, Iwao et al., "Bis(histamino)cyclodextrin-Zn-Imidazole Complex as an Artificial Carbonic Anhydrase", *J. Am. Chem. Soc.,* 106, pp. 4580-4584 (1984).

(Continued)

*Primary Examiner*—Leigh C. Maier
(74) *Attorney, Agent, or Firm*—Ropes & Gray LLP

(57) ABSTRACT

A method of preparing a supramolecular complex containing at least one therapeutic agent and a multi-dimensional polymer network is described. A supramolecular complex prepared by a method of the invention is described. A method of treatment by administering a therapeutically effective amount of a supramolecular complex of the invention is also described. Such a supramolecular complex may be used as a delivery vehicle for various therapeutic agents.

34 Claims, 7 Drawing Sheets

OTHER PUBLICATIONS

Tabushi, Iwao et al., "Characterization of Regiospecific A,C- and A,D-Disulfonate Capping of β-Cyclodextrin. Capping as an Efficient Production Technique", *J. Am. Chem. Soc.*, 106, pp. 5267-5270 (1984).

Lowry, Oliver H. et al., "Protein Measurement with the Folin Phenol Reagant", *The Journal of Biological Chemistry*, 193, pp. 265-275 (1951).

Mungall, William S. et al. "Use of the Azido Group in the Synthesis of 5' Terminal Aminodeoxythymidine Oligonucleotides", *J. Org. Chem*, 40, No. 11, pp. 1659-1162 (1975).

Hisamatsu, Makato et al., "Study on Specific Modification of Glucosyl Cyclodextrins", *Starch/Stärke*, 44, No. 4, pp. 188-191 (1992).

Boussif, Otmane et al., "A Versatile Vector for Gene and Oligonucleotide Transfer Into Cells in Culture and In Vivo: Polyethylenimine", *Proc. Natl. Acad. Sci, USA*, 92, pp. 7297-7301 (Aug. 1995).

Fieser, Mary et al., *Reagents for Organic Synthesis*, 3, pp. 265-266, Wiley, New York, 1967.

Cserháti, Tibor, "Charge-Transfer Chromatographic Study of the Complex Formation of Some Anticancer Drugs with γ-Cyclodextrin", *Analytical Biochemistry*, 225, pp. 328-332 (1995).

Melton, L.D. et al., "Synthesis of Monosubstituted Cyclohexaamyloses", *Carbohydrate Research*, 18, No. 1, pp. 29-37 (May 1971).

Fujita Kahee et al., "Guest-Induced Conformational Change of β-Cyclodextrin Capped With an Environmentally Sensitive Chromophore", *Bioorganic Chemistry*, 11, pp. 72-84 (1982).

Fujita, Kahee et al., "Selective Recognition of Alkanoates by a β-Cyclodextrin Flexibly Capped With a Chromophore", *Bioorganic Chemistry*, 11, pp. 108-114 (1982).

Hector Gonzalez, et al., "New Class of Polymers for the Delivery of Macromolecular Therapeutics," *Bioconjugate Chem.*, 10, 1068-1074 (1999).

Gonzalez, et al., "New Class of Polymers for the Delivery of Macromolecular Therapeutics," *Bioconjugate Chem.*, vol. 10, No. 6, pp. 1068-1074 (1999), (WEB Publ. on Sep. 24, 1999).

Hwang et al., "Effects of Structure of β-Cyclodextrin-Containing Polymers on Gene Delivery," *Bioconjugate Chem.*, vol. 12, No. 2, pp. 280-290 (2001), (WEB Publ. on Feb. 16, 2001).

Ooya, et al., "Synthesis and Characterization of an Oligopeptide-terminated Polyrotaxane as a Drug Carrier," *Polym. Adv. Technol.*, vol. 11, pp. 642-651 (2000).

Pun, et al., "Development of a Nonviral Gene Delivery Vehicle for Systemic Application," *Bioconjugate Chem.*, vol. 13, pp. 630-639, (2002), (WEB Publ. on Apr. 20, 2002).

"The Merck Index 11th Edition" *Merck Research Laboratories*, Whitehouse Station NJ XP002207314 p. 24, right-hand column, line 2-24 (1989).

"The Merck Index 11th Edition" *Merck Research Laboratories*, Whitehouse Station NJ XP002207313, p. 60, right-hand column, line 27—p. 61, left-hand column, line 8 (1989).

Smith, D., et al., "Nitric Oxide-Releasing Polymers Containing the [N(O)NO] Group", J. Med. Chem. 1996, 39, 1148-1156.

\* cited by examiner

Crosslinking of PEI 25kD

|   | 1 | 2 | 3 | 4 | 5 | 6 | 7 |
|---|---|---|---|---|---|---|---|
| % Crosslinker | | | 125 | 125 | 125 | 250 | 250 |
| Addition of heparan sulfate | | | | ✓ | ✓ | ✓ | ✓ |
| Addition of reducing agent | | | | | ✓ | | ✓ |

Figure 1

METHOD OF PREPARING A SUPRAMOLECULAR COMPLEX CONTAINING A THERAPEUTIC AGENT AND A MULTI-DIMENSIONAL POLYMER NETWORK

CROSS REFERENCE TO RELATED APPLICATIONS

This application claims benefit of priority under 35 U.S.C. § 119(e) to U.S. Provisional Application No. 60/110,847 filed Dec. 4, 1998 and to U.S. Provisional Application No. 60/127,856 filed Apr. 5, 1999, each of which is incorporated by reference in its entirety.

FIELD OF THE INVENTION

The invention relates to a method of preparing a supramolecular complex containing at least one therapeutic agent (e.g. DNA) and a multi-dimensional polymer network. Such a supramolecular complex may be used as a delivery vehicle of a therapeutic agent.

BACKGROUND OF THE INVENTION

Cyclodextrins are cyclic polysaccharides containing naturally occurring D(+)-glucopyranose units in an α-(1,4) linkage. The most common cyclodextrins are alpha (α)-cyclodextrins, beta (β)-cyclodextrins and gamma (γ)-cyclodextrins which contain, respectively, six, seven or eight glucopyranose units. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. Thus, using (β)-cyclodextrin as an example, a cyclodextrin is often represented schematically as follows:

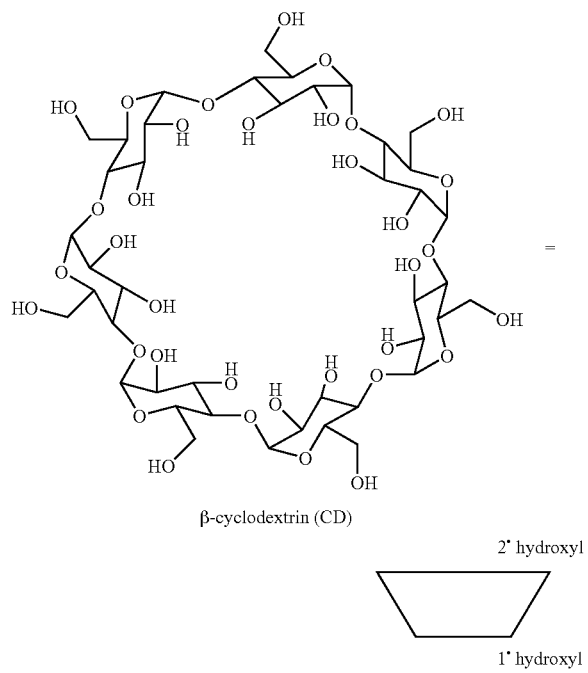

The side on which the secondary hydroxyl groups are located has a wider diameter than the side on which the primary hydroxyl groups are located. The hydrophobic nature of the cyclodextrin inner cavity allows for the inclusion of a variety of compounds. (*Comprehensive Supramolecular Chemistry*, Volume 3, J. L. Atwood et al., eds., Pergamon Press (1996); T. Cserhati, *Analytical Biochemistry*, 225:328-332 (1995); Husain et al., *Applied Spectroscopy*, 46:652-658 (1992); FR 2 665 169).

Cyclodextrins have been used as a delivery vehicle of various therapeutic compounds by forming inclusion complexes with various drugs that can fit into the hydrophobic cavity of the cyclodextrin or by forming non-covalent association complexes with other biologically active molecules such as oligonucleotides and derivatives thereof. For example, U.S. Pat. No. 4,727,064 describes pharmaceutical preparations consisting of a drug with substantially low water solubility and an amorphous, water-soluble cyclodextrin-based mixture. The drug forms an inclusion complex with the cyclodextrins of the mixture. In U.S. Pat. No. 5,691,316, a cyclodextrin cellular delivery system for oligonucleotides is described. In such a system, an oligonucleotide is noncovalently complexed with a cyclodextrin or, alternatively, the oligonucleotide may be covalently bound to adamantine which in turn is non-covalently associated with a cyclodextrin.

Various cyclodextrin containing polymers and methods of their preparation are also known in the art. (*Comprehensive Supramolecular Chemistry*, Volume 3, J. L. Atwood et al., eds., Pergamon Press (1996)). A process for producing a polymer containing immobilized cyclodextrin is described in U.S. Pat. No. 5,608,015. According to the process, a cyclodextrin derivative is reacted with either an acid halide monomer of an α,β-unsaturated acid or derivative thereof or with an α,β-unsaturated acid or derivative thereof having a terminal isocyanate group or a derivative thereof. The cyclodextrin derivative is obtained by reacting cyclodextrin with such compounds as carbonyl halides and acid anhydrides. The resulting polymer contains cyclodextrin units as side chains off a linear polymer main chain.

U.S. Pat. No. 5,276,088 describes a method of synthesizing cyclodextrin polymers by either reacting polyvinyl alcohol or cellulose or derivatives thereof with cyclodextrin derivatives or by copolymerization of a cyclodextrin derivative with vinyl acetate or methyl methacrylate. Again, the resulting cyclodextrin polymer contains a cyclodextrin moiety as a pendant moiety off the main chain of the polymer.

A biodegradable medicinal polymer assembly with supermolecular structure is described in WO 96/09073 A1 and U.S. Pat. No. 5,855,900. The assembly comprises a number of drug-carrying cyclic compounds prepared by binding a drug to an α, β, or γ-cyclodextrin and then stringing the drug/cyclodextrin compounds along a linear polymer with the biodegradable moieties bound to both ends of the polymer. Such an assembly is reportably capable of releasing a drug in response to a specific biodegradation occurring in a disease. These assemblies are commonly referred to as "necklace-type" cyclodextrin polymers.

SUMMARY OF THE INVENTION

The invention provides a method of preparing a supramolecular complex comprising at least one therapeutic agent and a multi-dimensional polymer network. According to such a method, at least one therapeutic agent is contacted with at least one polymer to form a composite. The polymer of the composite is then treated under conditions sufficient to form a supramolecular complex containing the therapeutic agent and a multi-dimensional polymer network.

The invention also provides a supramolecular complex containing at least one therapeutic agent and a multi-dimensional polymer network.

The invention further provides a method of treatment by administering a therapeutically effective amount of a supramolecular complex containing at least one therapeutic agent and a multi-dimensional polymer network.

BRIEF DESCRIPTION OF DRAWINGS

FIG. 1. Agarose Gel of Reversible Crosslinking of Branched PEI (25 kD) with DTBP.

DETAILED DESCRIPTION OF THE INVENTION

Figure 2A:
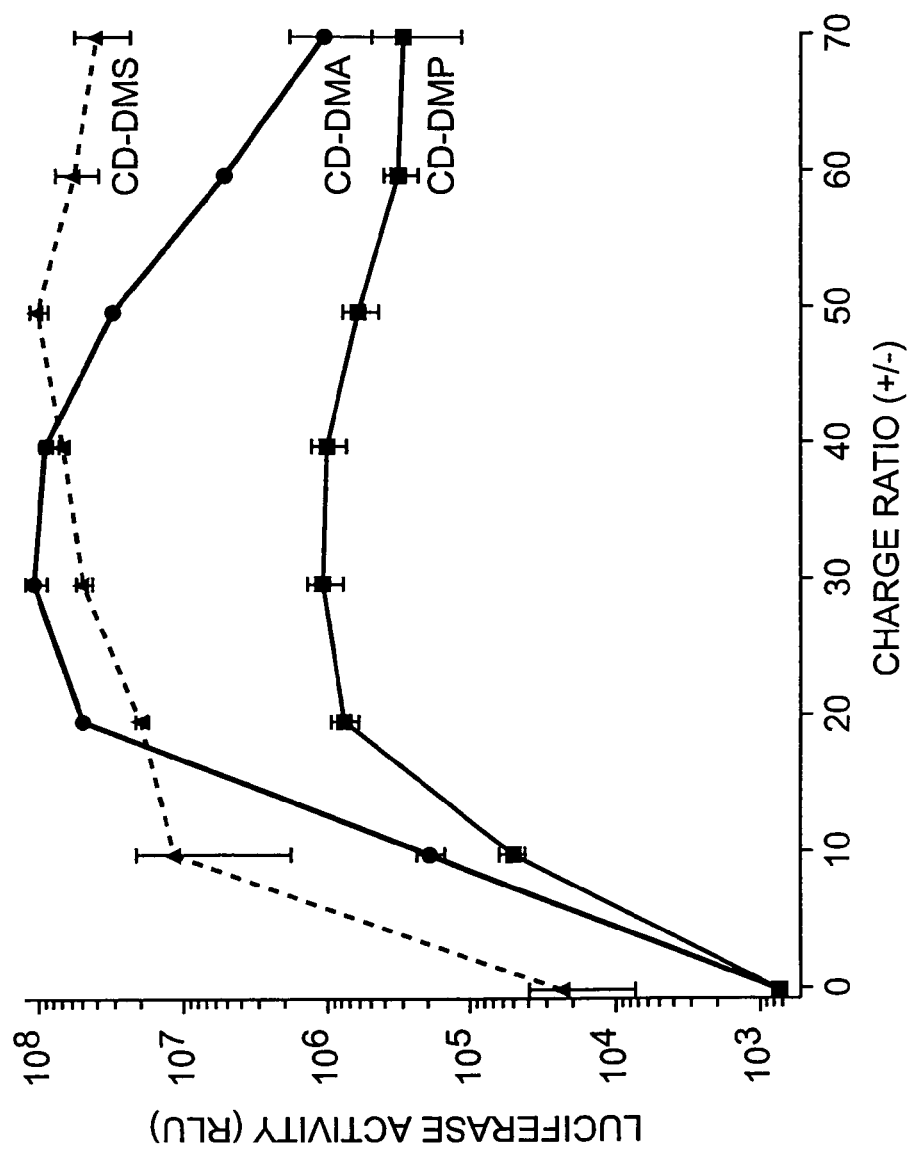
FIG. 2. Transfection Studies with Plasmids Encoding Luciferase Reporting Gene
  A. Transfection With CD-DMS, CD-DMA, and CD-DMP
  B. Toxicity of CD-DMS, CD-DMA, and CD-DMP
  C. Transfection to BHK-21 Cells (serum free) with CD-DMS and CD-DTBP
  D. Toxicity of CD-DMS and CD-DTBP with BHK-21 Cells (serum free)
Figure 2B:
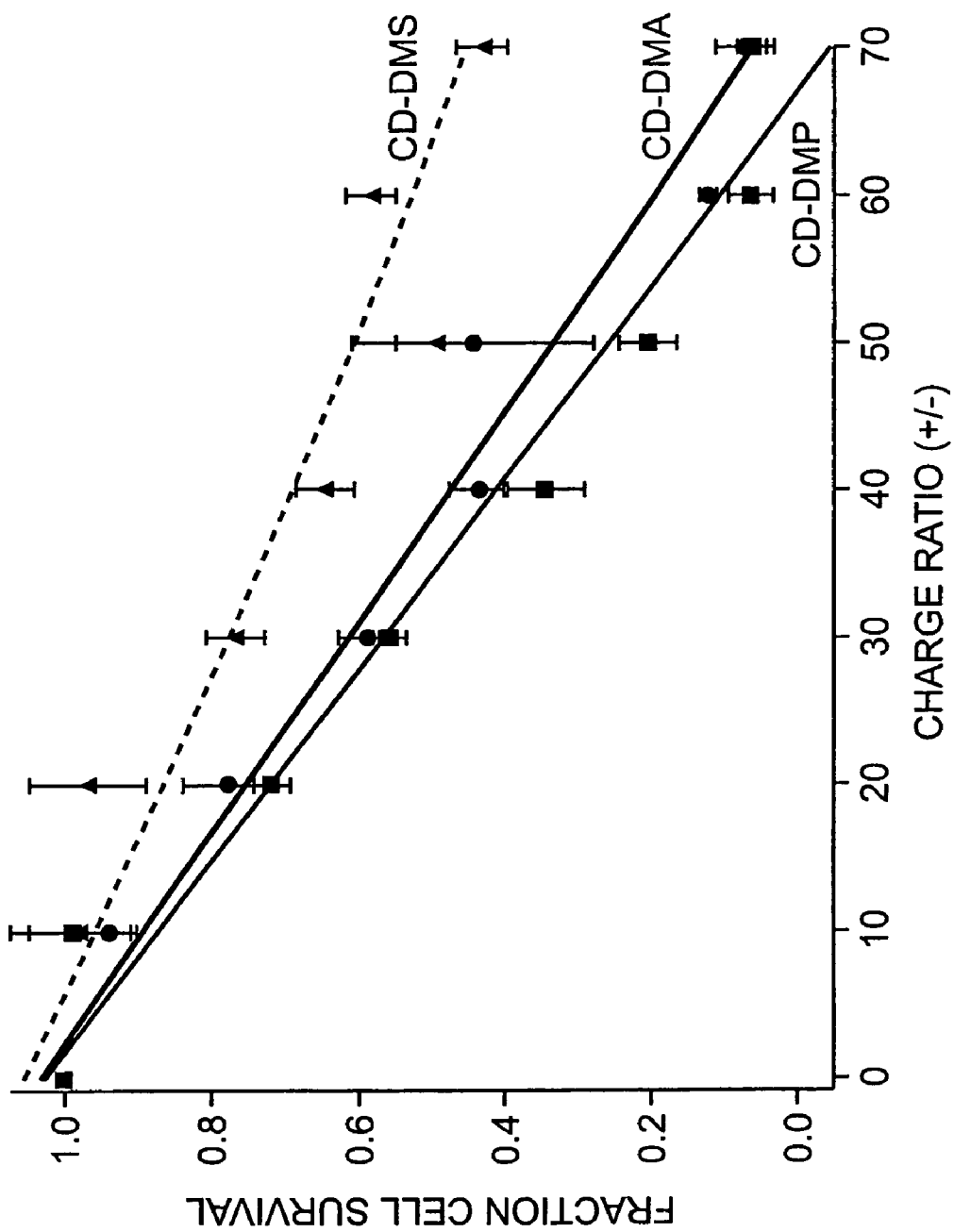
Figure 2C:
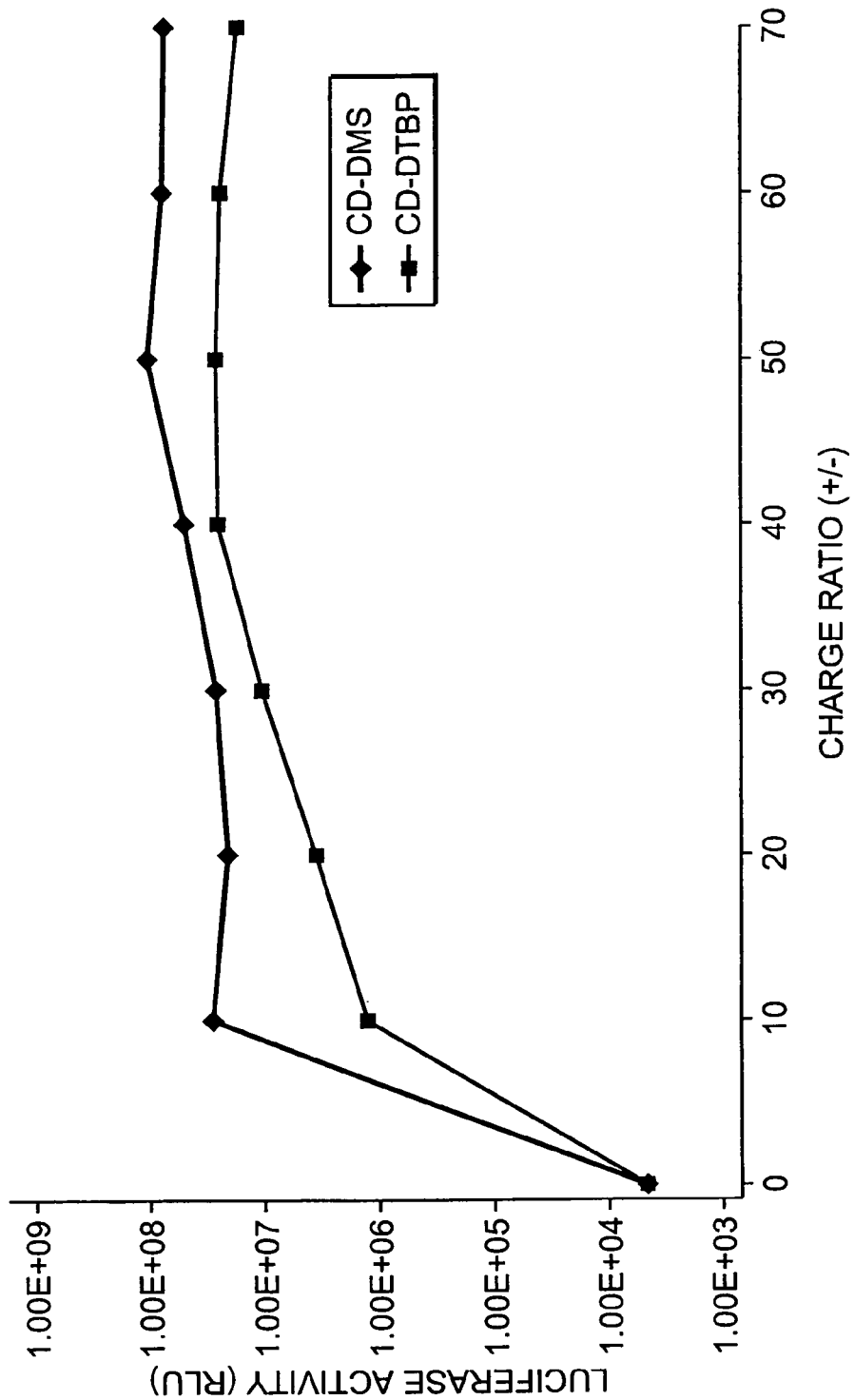
Figure 2D:
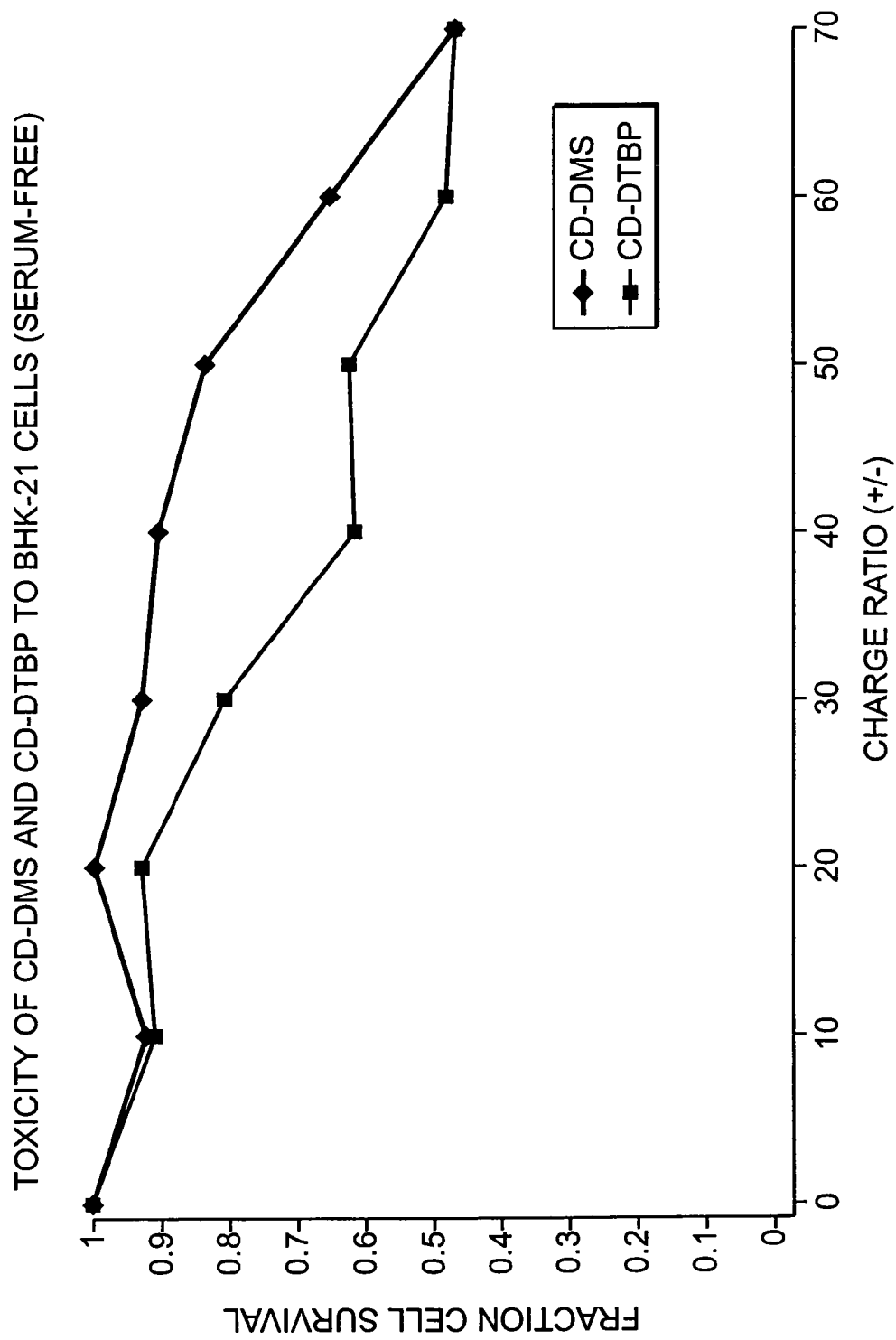

The invention relates to a method of preparing a supramolecular complex containing at least one therapeutic agent and a multi-dimensional polymer network. According to a method of the invention, at least one therapeutic agent is contacted with at least one polymer to form a composite and then the polymer of the composite is treated under conditions sufficient to form a supramolecular complex containing the therapeutic agent and a multi-dimensional polymer network.

A composite of at least one therapeutic agent and at least one polymer may be defined as a combination or integration of at least one therapeutic agent and at least one polymer, each as described below. According to the invention, a "polymer" is defined as either a single polymer molecule (e.g. a single polymer strand or fragment) or as a group of two or more polymer molecules (e.g. a group of two or more polymer strands or fragments). Thus, according to the invention, a composite contains at least one single polymer molecule; at least one group of two or more polymer molecules, which may be the same or different; or a mixture of at least one single polymer molecule and at least one group of two or more polymer molecules, which may be the same or different. A polymer molecule may be linear or branched. Accordingly, a group of two or more polymer molecules may be linear, branched, or a mixture of linear and branched polymers. According to the invention, prior to formation of the composite, the polymer of the composite does not exist as a substantially associated structure such as, for example, a polymer gel. However, the polymer as part of the composite, depending upon the nature of the polymers and the therapeutic agent, may form such a substantially associated structure. Each polymer of the composite may further contain or may be further modified to contain at least one functional group through which association of the polymers of the composite may be achieved, as described below.

The composite may be prepared by any suitable means known in the art. For example, the composite may be formed by simply contacting, mixing or dispersing a therapeutic agent with a polymer, each as described herein. A composite may also be prepared by polymerizing monomers, which may be the same or different, capable of forming a linear or branched polymer in the presence of a therapeutic agent. In a preferred embodiment of the invention, a composite may be prepared by polymerizing monomers, which may be the same or different, capable of forming a linear or branched polymer in the presence of a therapeutic agent where the therapeutic agent acts as a template for the polymerization. Trubetskoy et al., *Nucleic Acids Research*, Vol. 26, No. 18, pp. 4178-4185 (1998). The composite may be further modified with at least one ligand, as described below. The ligand may be introduced upon or after formation of the composite via ligand modification of the therapeutic agent and/or the polymer of the composite, as described herein. The composite may take any suitable form and, preferably, is in the form of particles.

According to the invention, the polymer of the composite is treated under conditions sufficient to form a supramolecular complex comprising a therapeutic agent and a (multi-dimensional polymer network, each as described herein. "Treatment of the polymer of the composite under conditions sufficient to form a supramolecular complex" may be defined as any suitable reaction condition(s), including the addition of additional agents or reactants, that promote association of the polymer of the composite. The polymer, as described above, may be associated via interpolymer covalent bonds, noncovalent bonds (e.g. ionic bonds), or noncovalent interactions (e.g. van der Waals interactions). Association via intrapolymer covalent bonding, noncovalent bonding, or noncovalent interactions of the polymer may occur as well. As a result of such association, the polymer of the composite interacts to form a multi-dimensional polymer network. Formation of a multi-dimensional polymer network may be determined using spectroscopy. A multi-dimensional polymer network exhibits different spectrographic data (e.g. infrared spectroscopy, nuclear magnetic resonance (NMR) spectroscopy) than the unassociated polymer of the composite. In addition, a multi-dimensional network of at least two polymers has an average molecular weight greater than that of the individual polymers of the composite.

In a preferred embodiment of the invention, "treatment of the polymer of the composite under conditions sufficient to form a supramolecular complex" involves crosslinking reaction conditions. For example, if the polymer of the composite is a single polymer molecule, the polymer may be reacted with a molecule(s), oligomer(s), or different polymer(s) that promotes crosslinking or forms crosslinks such that intrapolymer crosslinking of or actual crosslinking with the single polymer molecule of the composite results. Similarly, if the polymer of the composite is a group of two or more polymer molecules, the polymer may be reacted with a molecule(s), oligomer(s), or different polymer(s) that promotes crosslinking or forms crosslinks such that intrapolymer and/or interpolymer, preferably interpolymer, crosslinking of or actual crosslinking with the group of two or more polymer molecules of the composite results.

The crosslinking agent may be any crosslinking agent known in the art. The crosslinking agent may be any oligomer or polymer (e.g. polyethylene glycol (PEG) polymer, polyethylene polymer) capable of promoting crosslinking within or may be actually crosslinking with the polymer of the composite. The crosslinking oligomer or polymer may be the same or different as the polymer of the composite.

Likewise, the crosslinking agent may be any suitable molecule capable of crosslinking with the polymer of the composite.

Examples of crosslinking agents include dihydrazides and dithiols. In a preferred embodiment, the crosslinking agent is a labile group such that a crosslinked multi-dimensional polymer network may be uncrosslinked as desired. A mixture of different crosslinking agents may also be used. The different crosslinking agents may exhibit varying degrees of lability. Accordingly, the advantage of directed bioavailability (e.g. as in "timed release" formulations) may be achieved. Examples of suitable crosslinking agents include, but are not limited to, adipic acid dihydrazide, polyethylene glycol 600 ($PEG_{600}$) dihydrazide, dimethyl 3,3'-dithiobispropionimidate (DTBP), dithiobis(succinimidyl propionate) (DSP), disuccinimidyl suberate (DSS), and dimethylsuberimidate (DMS). The crosslinking agent may be further modified with at least one ligand as described herein.

"Treatment of the polymer of the composite under conditions sufficient to form a supramolecular complex" may also include suitable reaction conditions that promote the crosslinking of functional groups found on the polymer of the composite such that association via a new bond or interaction, as described above, results. The functional group may be any functional group known in the art which forms a new bond or interaction, as described above, under crosslinking reaction conditions. In a preferred embodiment of the invention, the polymer of the composite is functionalized with at least two thiol groups or may be modified to be functionalized with at least two thiol groups, which under appropriate oxidation conditions react to form a disulfide linkage. A thiol-functionalized polymer may be prepared by means known in the art including, for example, the addition of a thiolating reagent (e.g. Traut's Reagent, commercially available from Pierce Chemical Company, Rockford, Ill.). A thiol-functionalized polymer may also be prepared by polymerization of a protected-thiol monomer. After polymerization, the thiol groups may then be deprotected to give free thiol groups which may then be reacted under oxidation conditions to form a disulfide linkage(s). Suitable oxidation conditions include, for example, air oxidation and the use of an oxidizing reagent (e.g. ALDRITHIOL commercially available from Aldrich Chemical Company, Inc., Milwaukee, Wis.).

The degree of association, as described above, of the polymer of the composite forming the multi-dimensional polymer network may vary from partial association to complete association. By varying the degree of association of the polymer, a short chain polymer may be made to exhibit the characteristics of a long chain polymer while retaining the desired characteristics of a short chain polymer upon disassociation. For example, long chain polymer character promotes overall stability, i.e. resistance to degradation, until the target cell is reached while short chain polymer character promotes DNA release within the target cell. This duality affords a supramolecular complex containing at least one therapeutic agent and a multi-dimensional polymer network that exhibits greater stability in both nonphysiological and physiological conditions and greater shelf-life stability. Varying the degree of association of the polymer of the supramolecular complex also permits controlled release of the therapeutic agent.

In a preferred embodiment of the invention, the polymer of the composite is a substantially linear polymer. A substantially linear polymer may be any suitable substantially linear polymer or substantially linear copolymer known in the art capable as part of a composite of associating, preferably crosslinking, to form a multi-dimensional polymer network, as described above. According to the invention, a substantially linear polymer may be prepared by any means known in the art. Preferably, a substantially linear polymer may be prepared by any suitable polymerization technique known in the art including, but not limited to, those described in Trubetskoy et al., *Nucleic Acids Research*, Vol. 26, No. 18, pp 4178-4185 (1998) (e.g. template polymerization, step polymerization, chain polymerization). A substantially linear polymer may be prepared from a suitable monomer. Examples of suitable monomers for polymerization to form a substantially linear polymer include monomers such as, for example, bis(2-aminoethyl)-1,3-propanediamine (AEPD), and $N_2,N_2,N_3,N_3$-(3'-$PEG_{5000}$aminopropane)-bis(2-aminoethyl)-1,3-propanediammonium di-trifluoroacetate (AEPD-PEG). The substantially linear polymer may further contain or may be further modified to contain a functional group (e.g. thiol group), as described above. Preferably, the substantially linear polymer is linear polyethyleneimine (PEI) or a linear cyclodextrin-containing polymer, more preferably, a linear cyclodextrin-containing polymer. A linear cyclodextrin-containing polymer may be any water-soluble linear polymer containing at least one cyclodextrin moiety as part of the polymer backbone. More preferably, the linear cyclodextrin-containing polymer is a linear cyclodextrin copolymer or a linear oxidized cyclodextrin copolymer, each as described below.

A linear cyclodextrin copolymer is a polymer containing cyclodextrin moieties as an integral part of its polymer backbone. Previously, cyclodextrin moieties were not a part of the main polymer chain but rather attached off a polymer backbone as pendant moieties.

A linear cyclodextrin copolymer has a repeating unit of formula Ia, Ib, or a combination thereof:

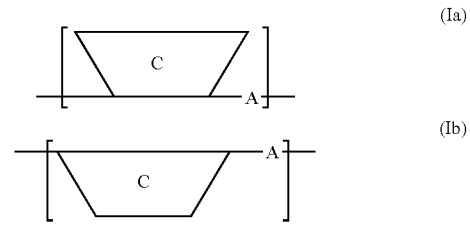

In formulae Ia and Ib, C is a substituted or unsubstituted cyclodextrin monomer and A is a comonomer bound, i.e. covalently bound, to cyclodextrin C. Polymerization of a cyclodextrin monomer C precursor with a comonomer A precursor results in a linear cyclodextrin copolymer. Within a single linear cyclodextrin copolymer, the cyclodextin monomer C unit may be the same or different and, likewise, the comonomer A may be the same or different.

A cyclodextrin monomer precursor may be any cyclodextrin or derivative thereof known in the art. As discussed above, a cyclodextrin is defined as a cyclic polysaccharide most commonly containing six to eight naturally occurring D(+)-glucopyranose units in an α-(1,4) linkage. Preferably, the cyclodextrin monomer precursor is a cyclodextrin having six, seven and eight glucose units, i.e., respectively, an alpha (α)-cyclodextrin, a beta (β)-cyclodextrin and a gamma (γ)-cyclodextrin. A cyclodextrin derivative may be any substituted cyclodextrin known in the art where the substituent does not interfere with copolymerization with comonomer A precursor as described below. A cyclodextrin derivative may be neutral, cationic or anionic. Examples of suitable substituents include, but are not limited to, hydroxyalkyl groups, such as, for example, hydroxypropyl, hydroxyethyl; ether groups, such as, for example, dihydroxypropyl ethers, methyl-hydroxyethyl ethers, ethyl-hydroxyethyl ethers, and ethyl-hydroxypropyl ethers; alkyl groups, such as, for example, methyl; saccharides, such as, for example, glucosyl and maltosyl; acid groups, such as, for example, carboxylic acids, phosphorous acids, phosphinous acids, phosphonic acids, phosphoric acids, thiophosphonic acids, and sulfonic acids; imidazole groups; sulfate groups; and protected thiol groups.

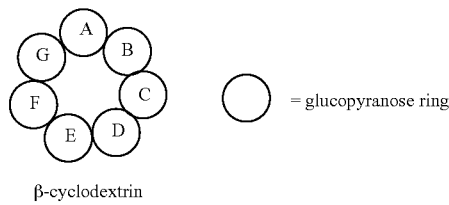

β-cyclodextrin

A cyclodextrin monomer precursor may be further chemically modified (e.g. halogenated, aminated) to facilitate or affect copolymerization of the cyclodextrin monomer precursor with a comonomer A precursor, as described below. Chemical modification of a cyclodextrin monomer precursor allows for polymerization at only two positions on each cyclodextrin moiety, i.e. the creation of a bifunctional cyclodextrin moiety. The numbering scheme for the C1-C6 positions of each glucopyranose ring is as follows:

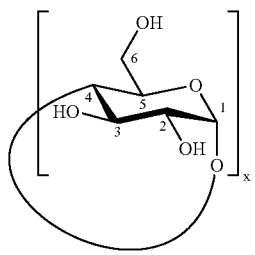

x = 6, 7 or 8

In a preferred embodiment, polymerization occurs at two of any C2, C3 and C6 position, including combinations thereof, of the cyclodextrin moiety. For example, one cyclodextrin monomer precursor may be polymerized at two C6 positions while another cyclodextrin monomer precursor may be polymerized at a C2 and a C6 position of the cyclodextrin moiety. Using β-cyclodextrin as an example, the lettering scheme for the relative position of each glucopyranose ring in a cyclodextrin is as follows:

In a preferred embodiment of a linear cyclodextrin copolymer, the cyclodextrin monomer C has the following general formula (II):

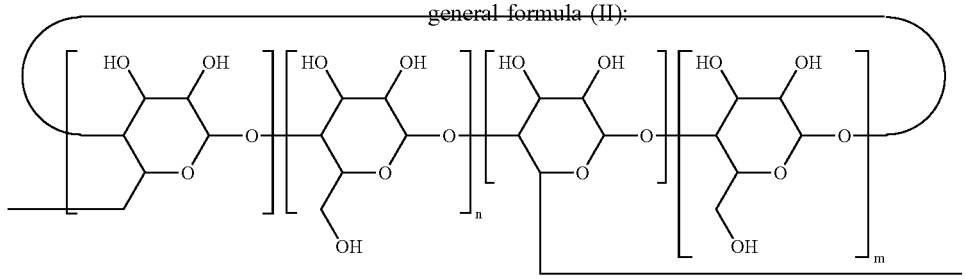

In formula (II), n and m represent integers which, along with the other two glucopyranose rings, define the total number of glucopyranose units in the cyclodextrin monomer. Formula (II) represents a cyclodextrin monomer which is capable of being polymerized at two C6 positions on the cyclodextrin unit. Examples of cyclodextrin monomers of formula (II) include, but are not limited to, $6^A,6^B$-dideoxy-α-cyclodextrin (n=0, m=4), $6^A,6^C$-dideoxy-α-cyclodextrin (n=1, m=3), $6^A,6^D$-dideoxy-α-cyclodextrin (n=2, m=2), $6^A,6^B$-dideoxy-β-cyclodextrin (n=0, m=5), $6^A,6^C$-dideoxy-β-cyclodextrin (n=1, m=4), $6^A,6^D$-dideoxy-β-cyclodextrin (n=2, m=3), $6^A,6^B$-dideoxy-γ-cyclodextrin (n=0, m=6), $6^A,6^C$-dideoxy-γ-cyclodextrin (n=1, m=5), $6^A,6^D$-dideoxy-γ-cyclodextrin (n=2, m=4), and $6^A,6^E$-dideoxy-γ-cyclodextrin (n=3, m=3). In another preferred embodiment of a linear cyclodextrin copolymer, a cyclodextrin monomer C unit has the following general formula (III):

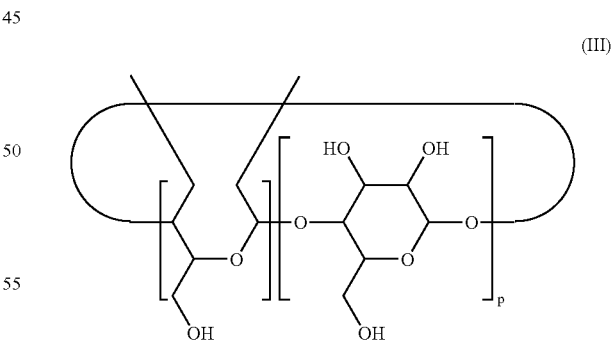

where p=5-7. In formula (II), at least one of D(+)-glucopyranose units of a cyclodextrin monomer has undergone ring opening to allow for polymerization at a C2 and a C3 position of the cyclodextrin unit. Cyclodextrin monomers of formula (III) such as, for example, $2^A,3^A$-diamino-$2^A,3^A$-dideoxy-β-cyclodextrin and $2^A,3^A$-dialdehyde-$2^A,3^A$-dideoxy-β-cyclodextrin are commercially available from Carbomer of Westborough, Mass. Examples of cyclodextrin monomers of formula (II) include, but are not limited to, $2^A,3^A$-dideoxy-$2^A,3^A$-dihydro-α-cyclodextrin, $2^A,3^A$-dideoxy-$2^A,3^A$-dihydro-β-cyclodextrin, $2^A,3^A$-dideoxy-$2^A,3^A$-dihydro-γ-cyclodextrin, commonly referred to as, respectively, 2,3-dideoxy-α-cyclodextrin, 2,3-dideoxy-β-cyclodextrin, and 2,3-dideoxy-γ-cyclodextrin.

A comonomer A precursor may be any straight chain or branched, symmetric or asymmetric compound which upon reaction with a cyclodextrin monomer precursor, as described above, links two cyclodextrin monomers together. Preferably, a comonomer A precursor is a compound containing at least two functional groups through which reaction and thus linkage of the cyclodextrin monomers can be achieved. Examples of possible functional groups, which may be the same or different, terminal or internal, of each comonomer A precursor include, but are not limited to, amino, acid, ester, imidazole, and acyl halide groups and derivatives thereof. In a preferred embodiment, the two functional groups are the same and terminal. Upon copolymerization of a comonomer A precursor with a cyclodextrin monomer precursor, two cyclodextrin monomers may be linked together by joining the primary hydroxyl side of one cyclodextrin monomer with the primary hydroxyl side of another cyclodextrin monomer, by joining the secondary hydroxyl side of one cyclodextrin monomer with the secondary hydroxyl side of another cyclodextrin monomer, or by joining the primary hydroxyl side of one cyclodextrin monomer with the secondary hydroxyl side of another cyclodextrin monomer. Accordingly, combinations of such linkages may exist in the final copolymer. Both the comonomer A precursor and the comonomer A of the final copolymer may be neutral, cationic (e.g. by containing protonated groups such as, for example, quaternary ammonium groups) or anionic (e.g. by containing deprotonated groups, such as, for example, sulfate, phosphate or carboxylate anionic groups). The counterion of a charged comonomer A precursor or comonomer A may be any suitable counteranion or countercation (e.g. the counteranion of a cationic comonomer A precursor or comonomer A may be a halide (e.g chloride) anion). The charge of comonomer A of the copolymer may be adjusted by adjusting pH conditions. Examples of suitable comonomer A precursors include, but are not limited to, cystamine, 1,6-diaminohexane, diimidazole, dithioimidazole, spermine, dithiospermine, dihistidine, dithiohistidine, succinimide (e.g. dithiobis(succinimidyl propionate) (DSP) and disuccinimidyl suberate (DSS)), and imidates (e.g. dimethyl 3,3'-dithiobispropion-imidate (DTBP)). Copolymerization of a comonomer A precursor with a cyclodextrin monomer precursor leads to the formation of a linear cyclodextrin copolymer containing comonomer A linkages of the following general formulae:

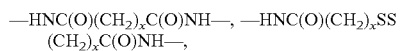
—HNC(O)(CH$_2$)$_x$C(O)NH—, —HNC(O)(CH$_2$)$_x$SS(CH$_2$)$_x$C(O)NH—,

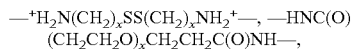
—$^+$H$_2$N(CH$_2$)$_x$SS(CH$_2$)$_x$NH$_2$$^+$—, —HNC(O)(CH$_2$CH$_2$O)$_x$CH$_2$CH$_2$C(O)NH—,

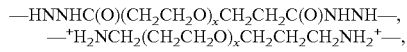
—HNNHC(O)(CH$_2$CH$_2$O)$_x$CH$_2$CH$_2$C(O)NHNH—,
—$^+$H$_2$NCH$_2$(CH$_2$CH$_2$O)$_x$CH$_2$CH$_2$CH$_2$NH$_2$$^+$—,

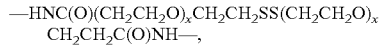
—HNC(O)(CH$_2$CH$_2$O)$_x$CH$_2$CH$_2$SS(CH$_2$CH$_2$O)$_x$CH$_2$CH$_2$C(O)NH—,

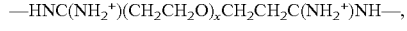
—HNC(NH$_2$$^+$)(CH$_2$CH$_2$O)$_x$CH$_2$CH$_2$C(NH$_2$$^+$)NH—,

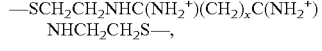
—SCH$_2$CH$_2$NHC(NH$_2$$^+$)(CH$_2$)$_x$C(NH$_2$$^+$)NHCH$_2$CH$_2$S—,

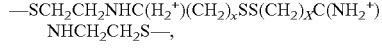
—SCH$_2$CH$_2$NHC(H$_2$$^+$)(CH$_2$)$_x$SS(CH$_2$)$_x$C(NH$_2$$^+$)NHCH$_2$CH$_2$S—,

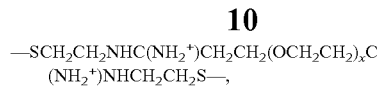
—SCH$_2$CH$_2$NHC(NH$_2$$^+$)CH$_2$CH$_2$(OCH$_2$CH$_2$)$_x$C(NH$_2$$^+$)NHCH$_2$CH$_2$S—,

—HNC(O)(CH$_2$CH$_2$O)$_y$(CHCH$_2$O)$_z$CH$_2$CH$_2$C(O)NH—

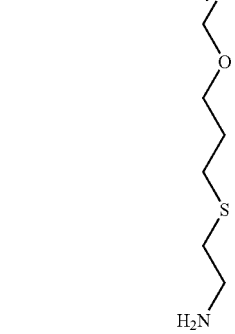

—HNC(O)(CH$_2$CH$_2$O)$_y$(CHCH$_2$O)$_z$CH$_2$CH$_2$C(O)NH—

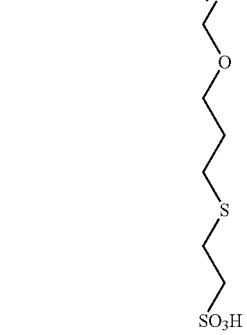

—HNC(O)(CH$_2$CH$_2$O)$_y$(CHCH$_2$O)$_z$CH$_2$CH$_2$C(O)NH—

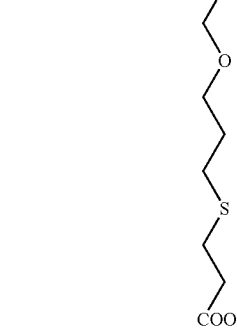

—HNC(O)(CH$_2$CH$_2$O)$_y$(CHCH$_2$O)$_z$CH$_2$CH$_2$C(O)NH—

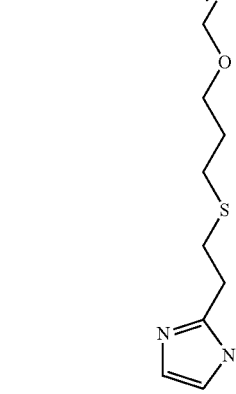

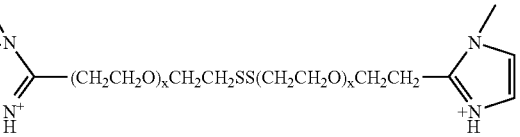

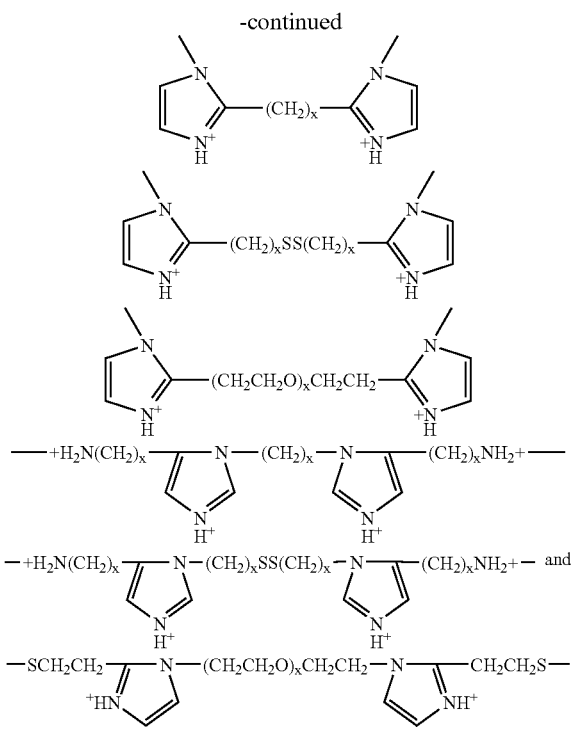

In the above formulae, x=1-50, and y+z=x. Preferably, x=1-30. More preferably, x=1-20. In a preferred embodiment, comonomer A is biodegradable or acid-labile. Also in a preferred embodiment, the comonomer A precursor and hence the comonomer A may be selectively chosen in order to achieve a desired application. For example, to deliver small molecular therapeutic agents, a charged polymer may not be necessary and the comonomer A may be a polyethylene glycol group.

In a preferred embodiment of the invention, a linear cyclodextrin copolymer may be prepared by copolymerizing a cyclodextrin monomer precursor disubstituted with an appropriate leaving group with a comonomer A precursor capable of displacing the leaving groups. The leaving group, which may be the same or different, may be any leaving group known in the art which may be displaced upon copolymerization with a comonomer A precursor. In a preferred embodiment, a linear cyclodextrin copolymer may be prepared by iodinating a cyclodextrin monomer precursor to form a diiodinated cyclodextrin monomer precursor and copolymerizing the diiodinated cyclodextrin monomer precursor with a comonomer A precursor to form a linear cyclodextrin copolymer having a repeating unit of formula Ia, Ib, or a combination thereof, each as described above. In a preferred embodiment, a method of preparing a linear cyclodextrin iodinates a cyclodextrin monomer precursor as described above to form a diiodinated cyclodextrin monomer precursor of formula IVa, IVb, IVc or a mixture thereof:

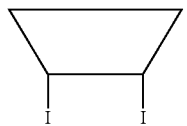

(IVa)

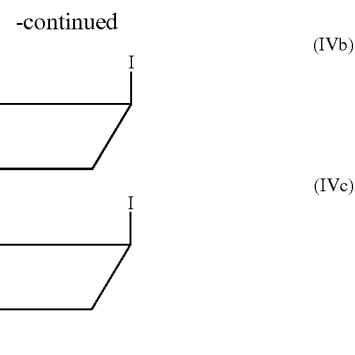

The diiodinated cyclodextrin may be prepared by any means known in the art (see, e.g., Tabushi et al. *J. Am. Chem.* 106, 5267-5270 (1984); Tabushi et al. *J. Am. Chem.* 106, 4580-4584 (1984)). For example, β-cyclodextrin may be reacted with biphenyl-4,4'-disulfonyl chloride in the presence of anhydrous pyridine to form a biphenyl-4,4'-disulfonyl chloride capped β-cyclodextrin which may then be reacted with potassium iodide to produce diiodo-β-cyclodextrin. The cyclodextrin monomer precursor is iodinated at only two positions. By copolymerizing the diiodinated cyclodextrin monomer precursor with a comonomer A precursor, as described above, a linear cyclodextrin polymer having a repeating unit of formula Ia, Ib, or a combination thereof, also as described above, may be prepared. If appropriate, the iodine or iodo groups may be replaced with other known leaving groups.

The iodo groups or other appropriate leaving group may be displaced with a group that permits reaction with a comonomer A precursor, as described above. For example, a diiodinated cyclodextrin monomer precursor of formula IVa, IVb, IVc or a mixture thereof may be aminated to form a diaminated cyclodextrin monomer precursor of formula Va, Vb, Vc or a mixture thereof:

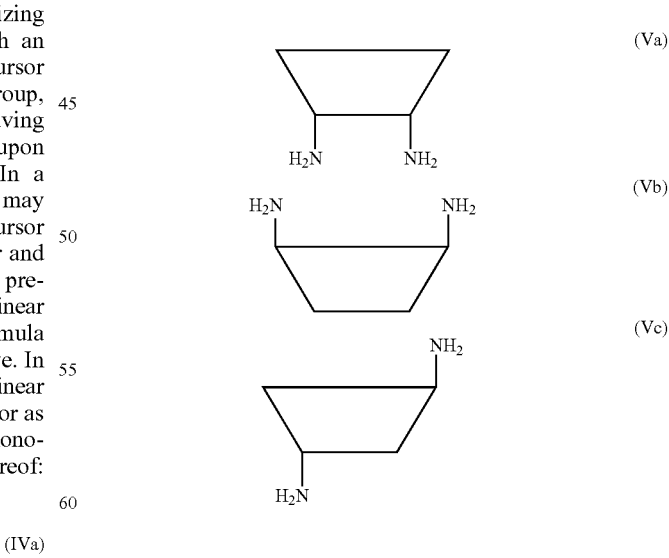

The diaminated cyclodextrin monomer precursor may be prepared by any means known in the art (see, e.g., Tabushi et al. *Tetrahedron Lett.* 18:1527-1530 (1977); Mungall et al., *J. Org. Chem.* 1659-1662 (1975)). For example, a diiodo-β-cyclodextrin may be reacted with sodium azide and then reduced to form a diamino-β-cyclodextrin. The cyclodextrin monomer precursor is aminated at only two positions. The diaminated cyclodextrin monomer precursor may then be copolymerized with a comonomer A precursor, as described above, to produce a linear cyclodextrin copolymer having a repeating unit of formula Ia, Ib, or a combination thereof, also as described above. However, the amino functionality of a diaminated cyclodextrin monomer precursor need not be directly attached to the cyclodextrin moiety. Alternatively, the amino functionality may be introduced by displacement of the iodo or other appropriate leaving groups of a cyclodextrin monomer precursor with amino group containing moieties such as, for example, $^-SCH_2CH_2NH_2$, to form a diaminated cyclodextrin monomer precursor of formula Vd, Ve, Vf or a mixture thereof:

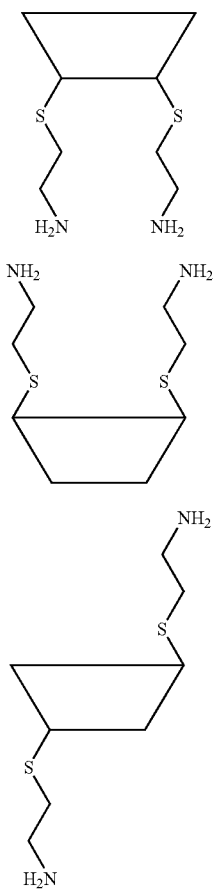

(Vd)

(Ve)

(Vf)

A linear cyclodextrin copolymer may also be prepared by reducing a linear oxidized cyclodextrin copolymer, as described below. This method may be performed as long as the comonomer A does not contain a reducible moiety or group such as, for example, a disulfide linkage.

A linear cyclodextrin copolymer may be oxidized so as to introduce at least one oxidized cyclodextrin monomer into the copolymer such that the oxidized cyclodextrin monomer is an integral part of the polymer backbone. A linear cyclodextrin copolymer which contains at least one oxidized cyclodextrin monomer is defined as a linear oxidized cyclodextrin copolymer. The cyclodextrin monomer may be oxidized on either the secondary or primary hydroxyl side of the cyclodextrin moiety. If more than one oxidized cyclodextrin monomer is present in a linear oxidized cyclodextrin copolymer, the same or different cyclodextrin monomers oxidized on either the primary hydroxyl side, the secondary hydroxyl side, or both may be present. For illustration purposes, a linear oxidized cyclodextrin copolymer with oxidized secondary hydroxyl groups has, for example, at least one unit of formula VIa or VIb:

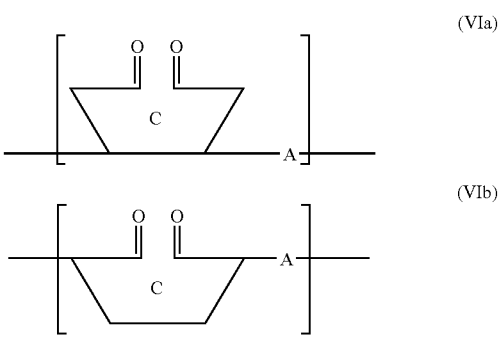

In formulae VIa and VIb, C is a substituted or unsubstituted oxidized cyclodextrin monomer and A is a comonomer bound, i.e. covalently bound, to the oxidized cyclodextrin C. Also in formulae VIa and VIb, oxidation of the secondary hydroxyl groups leads to ring opening of the cyclodextrin moiety and the formation of aldehyde groups.

A linear oxidized cyclodextrin copolymer may be prepared by oxidation of a linear cyclodextrin copolymer as discussed above. Oxidation of a linear cyclodextrin copolymer may be accomplished by oxidation techniques known in the art. (Hisamatsu et al., *Starch* 44:188-191 (1992)). Preferably, an oxidant such as, for example, sodium periodate is used. It would be understood by one of ordinary skill in the art that under standard oxidation conditions that the degree of oxidation may vary or be varied per copolymer. Thus in one embodiment, a linear oxidized copolymer may contain one oxidized cyclodextrin monomer. In another embodiment, substantially all to all cyclodextrin monomers of the copolymer would be oxidized.

Another method of preparing a linear oxidized cyclodextrin copolymer involves the oxidation of a diiodinated or diaminated cyclodextrin monomer precursor, as described above, to form an oxidized diiodinated or diaminated cyclodextrin monomer precursor and copolymerization of the oxidized diiodinated or diaminated cyclodextrin monomer precursor with a comonomer A precursor. In a preferred embodiment, an oxidized diiodinated cyclodextrin monomer precursor of formula VIIa, VIIb, VIIc, or a mixture thereof:

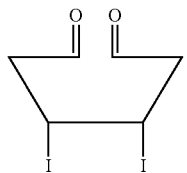

(VIIa)

-continued (VIIb)

(VIIc)

may be prepared by oxidation of a diiodinated cyclodextrin monomer precursor of formulae IVa, IVb, IVc, or a mixture thereof, as described above. In another preferred embodiment, an oxidized diaminated cyclodextrin monomer precursor of formula VIIIa, VIIIb, VIIIc or a mixture thereof:

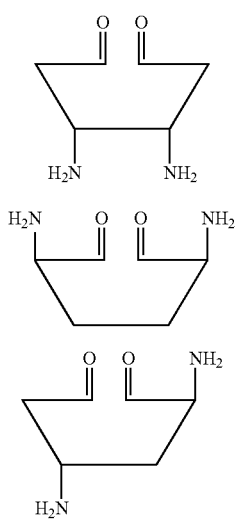

(VIIIa)

(VIIIb)

(VIIIc)

may be prepared by amination of an oxidized diiodinated cyclodextrin monomer precursor of formulae VIIa, VIIb, VIIc, or a mixture thereof, as described above. In still another preferred embodiment, an oxidized diaminated cyclodextrin monomer precursor of formula IXa, IXb, IXc or a mixture thereof:

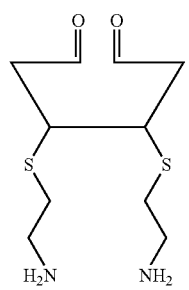

(IXa)

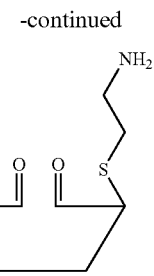

(IXb)

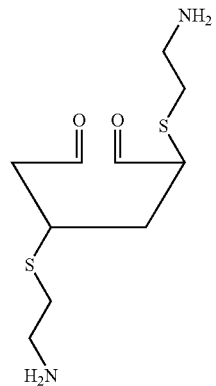

(IXc)

may be prepared by displacement of the iodo or other appropriate leaving groups of an oxidized cyclodextrin monomer precursor disubstituted with an iodo or other appropriate leaving group with the amino group containing moiety $^-SCH_2CH_2NH_2$.

Alternatively, an oxidized diiodinated or diaminated cyclodextrin monomer precursor, as described above, may be prepared by oxidizing a cyclodextrin monomer precursor to form an oxidized cyclodextrin monomer precursor and then diiodinating and/or diaminating the oxidized cyclodextrin monomer, as described above. As discussed above, the cyclodextrin moiety may be modified with other leaving groups other than iodo groups and other amino group containing functionalities. The oxidized diiodinated or diaminated cyclodextrin monomer precursor may then be copolymerized with a comonomer A precursor, as described above, to form a linear oxidized cyclodextrin copolymer.

In a preferred embodiment of the invention, a linear cyclodextrin copolymer or a linear oxidized cyclodextrin copolymer terminates with at least one comonomer A precursor or hydrolyzed product of the comonomer A precursor, each as described above. As a result of termination of the cyclodextrin copolymer with at least one comonomer A precursor, at least one free functional group, as described above, exists per linear cyclodextrin copolymer or per linear oxidized cyclodextrin copolymer. For example, the functional group may be an acid group or a functional group that may be hydrolyzed to an acid group. According to the invention, the functional group may be further chemically modified as desired to enhance the properties of the cyclodextrin copolymer, such as, for example, colloidal stability and transfection efficiency. For example, the functional group may be modified by reaction with PEG to form a PEG terminated cyclodextrin copolymer to enhance colloidal stability or with histidine to form an imidazolyl terminated cyclodextrin copolymer to enhance intracellular (e.g. endosomal release) and transfection efficiency.

Further chemistry may be performed on the cyclodextrin copolymer through the modified functional group. For example, the modified functional group may be used to extend a polymer chain by linking a linear cyclodextrin copolymer or linear oxidized cyclodextrin copolymer, as described herein, to the same or different cyclodextrin copolymer or to a non-cyclodextrin polymer. In a preferred embodiment of the invention, the polymer to be added on is the same or different linear cyclodextrin copolymer or linear oxidized cyclodextrin copolymer which may also terminate with at least one comonomer A precursor for further modification, each as described herein.

Alternatively, at least two of the same or different linear cyclodextrin copolymers or linear oxidized cyclodextrin copolymers containing a terminal functional group or a terminal modified functional group, as described above, may be reacted and linked together through the functional or modified functional group. Preferably, upon reaction of the functional or modified functional groups, a degradable moiety such as, for example, a disulfide linkage is formed. For example, modification of the terminal functional group with cysteine may be used to produce a linear cyclodextrin copolymer or linear oxidized cyclodextrin copolymer having at least one free thiol group. Reaction with the same or different cyclodextrin copolymer also containing at least one free thiol group will form a disulfide linkage between the two copolymers. In a preferred embodiment of the invention, the functional or modified functional groups may be selected to offer linkages exhibiting different rates of degradation (e.g. via enzymatic degradation) and thereby provide, if desired, a time release system for a therapeutic agent. The resulting polymer may be crosslinked, as described herein. A therapeutic agent, as described herein, may be added prior to or post crosslinking of the polymer. A ligand, as described herein, may also be bound through the modified functional group.

According to the invention, a linear cyclodextrin copolymer or linear oxidized cyclodextrin copolymer may be attached to or grafted onto a substrate. The substrate may be any substrate as recognized by those of ordinary skill in the art. In another preferred embodiment of the invention, a linear cyclodextrin copolymer or linear oxidized cyclodextrin copolymer may be crosslinked to a polymer to form, respectively, a crosslinked cyclodextrin copolymer or a crosslinked oxidized cyclodextrin copolymer. The polymer may be any polymer capable of crosslinking with a linear or linear oxidized cyclodextrin copolymer of the invention (e.g. polyethylene glycol (PEG) polymer, polyethylene polymer). The polymer may also be the same or different linear cyclodextrin copolymer or linear oxidized cyclodextrin copolymer. Thus, for example, a linear cyclodextrin copolymer may be crosslinked to any polymer including, but not limited to, itself, another linear cyclodextrin copolymer, and a linear oxidized cyclodextrin copolymer. A crosslinked linear cyclodextrin copolymer of the invention may be prepared by reacting a linear cyclodextrin copolymer with a polymer in the presence of a crosslinking agent. A crosslinked linear oxidized cyclodextrin copolymer of the invention may be prepared by reacting a linear oxidized cyclodextrin copolymer with a polymer in the presence of an appropriate crosslinking agent. The crosslinking agent may be any crosslinking agent known in the art. Examples of crosslinking agents include dihydrazides and dithiols. In a preferred embodiment, the crosslinking agent is a labile group such that a crosslinked copolymer may be uncrosslinked if desired.

A linear cyclodextrin copolymer and a linear oxidized cyclodextrin copolymer of the invention may be characterized by any means known in the art. Such characterization methods or techniques include, but are not limited to, gel permeation chromatography (GPC), matrix assisted laser desorption ionization-time of flight mass spectrometry (MALDI-TOF Mass spec), $^1$H and $^{13}$C NMR, light scattering and titration.

In another preferred embodiment of the invention, the polymer of the composite is a substantially branched polymer such as, for example, branched polyethyleneimine (PEI) or a branched cyclodextrin-containing polymer, preferably, a branched cyclodextrin-containing polymer. A branched cyclodextrin-containing polymer may be any water-soluble branched polymer containing at least one cyclodextrin moiety which may be a part of the polymer backbone and/or pendant from the polymer backbone. Preferably, a branched cyclodextrin-containing polymer is a branched cyclodextrin copolymer or a branched oxidized cyclodextrin copolymer. A branched cyclodextrin copolymer or a branched oxidized cyclodextrin copolymer is, respectively, a linear cyclodextrin copolymer or a linear oxidized cyclodextrin copolymer, as described above, from which a subordinate chain is branched. The branching subordinate chain may be any saturated or unsaturated, linear or branched hydrocarbon chain. The branching subordinate chain may further contain various functional groups or substituents such as, for example, hydroxyl, amino, acid, ester, amido, keto, formyl, and nitro groups. The branching subordinate chain may also contain at least one cyclodextrin moiety. The branching subordinate chain may also be modified with a ligand, as described herein. Such ligand modification includes, but is not limited to, attachment of a ligand to a cyclodextrin moiety in the branching subordinate chain. Preferably, the branched cyclodextrin-containing polymer is a branched cyclodextrin copolymer or a branched oxidized cyclodextrin copolymer, as defined above, of which the branching subordinate chain contains at least one cyclodextrin moiety. According to the invention, if the branching subordinate chain contains at least one cyclodextrin moiety, the cyclodextrin moiety may facilitate encapsulation of a therapeutic agent, each as described herein. Preferably, a cyclodextrin moiety of a branching subordinate chain facilitates encapsulation of a therapeutic agent in conjunction with a cyclodextrin moiety in the polymer backbone. A branched cyclodextrin-containing polymer may be prepared by any means known in the art including, but not limited to, derivatization (e.g. substitution) of a polymer (e.g. linear or branched PEI) with a cyclodextrin monomer precursor, as defined above. A branched cyclodextrin-containing polymer of the invention may be characterized by any means known in the art. Such characterization methods or techniques include, but are not limited to, gel permeation chromatography (GPC), matrix assisted laser desorption ionization-time of flight mass spectrometry (MALDI-TOF Mass spec), $^1$H and $^{13}$C NMR, light scattering and titration.

According to the invention, a branched cyclodextrin-containing polymer may be crosslinked under crosslinking reaction conditions, each as described above. In a preferred embodiment of the invention, a branched cyclodextrin-containing polymer is crosslinked with itself. In another preferred embodiment of the invention, a branched cyclodextrin-containing polymer is crosslinked with a polymer. The polymer may be the same or different branched cyclodextrin-containing polymer, a substantially linear polymer, or a substantially branched polymer, each as described above.

According to the invention, a substantially branched polymer may be attached to or grafted onto a substrate, as described above. Further chemistry may be performed on the substantially branched polymer through a modified functional group, as described above.

A poly(ethylenimine) (PEI) for use in the invention has a weight average molecular weight of between about 800 and about 800,000 daltons, preferably, between about 2,000 and 100,000 daltons, more preferably, between about 2,000 and about 25,000 daltons. The PEI may be linear or branched. Suitable PEI compounds are commercially available from many sources, including polyethylenimine from Aldrich Chemical Company, polyethylenimine from Polysciences, and POLYMIN poly(ethylenimine) and LUPASOL™ poly (ethylenimine) available from BASF Corporation.

According to the invention, a polymer of the composite, or one of the monomers which form a polymer of the composite, may be modified with at least one ligand such that the resulting composite or supramolecular complex is associated with at least one ligand, each as described herein. Alternatively, according to a method of the invention, once a composite or a supramolecular complex is formed, it may then be contacted with a ligand such that the composite or supramolecular complex is modified with at least one ligand in such a way that the ligand is associated with the composite or supramolecular complex, each as described herein. The ligand of such a ligand-containing composite or ligand-containing supramolecular complex allows for targeting and/or binding to a desired cell. If more than one ligand is attached, the ligand may be the same or different. Examples of suitable ligands include, but are not limited to, vitamins (e.g. folic acid), proteins (e.g. transferrin, and monoclonal antibodies) and polysaccharides. The choice of ligand may vary depending upon the type of delivery desired. For example, receptor-mediated delivery may by achieved by, but not limited to, the use of a folic acid ligand while antisense oligo delivery may be achieved by, but not limited to, use of a transferrin ligand.

The ligand may be associated with the composite or supramolecular complex by means known in the art. For example, a linear cyclodextrin copolymer or linear oxidized cyclodextrin copolymer may be modified with at least one ligand attached to the cyclodextrin copolymer. The ligand may be attached to the cyclodextrin copolymer through the cyclodextrin monomer C or comonomer A. Preferably, the ligand is attached to at least one cyclodextrin moiety of the cyclodextrin copolymer. Preferably, the ligand allows a cyclodextrin copolymer to target and bind to a cell. If more than one ligand, which may be the same or different, is attached to a cyclodextrin copolymer, the additional ligand or ligands may be bound to the same or different cyclodextrin moiety or the same or different comonomer A of the copolymer. A cyclodextrin copolymer may also be further modified to contain a functional group to promote association of the cyclodextrin copolymer with the therapeutic agent and/or other polymer(s) of the composite.

According to a method of the invention, upon formation of the supramolecular complex, the therapeutic agent becomes encapsulated in the multi-dimensional polymer network created from the polymer of a composite, as described above. Encapsulation is defined as any means by which the therapeutic agent associates (e.g. electrostatic interaction, hydrophobic interaction, actual encapsulation) with the multi-dimensional polymer network. The degree of association may be determined by techniques known in the art including, for example, fluorescence studies, DNA mobility studies, light scattering, electron microscopy, and will vary depending upon the therapeutic agent. As a mode of delivery, for example, a supramolecular complex containing a multi-dimensional polymer network created from the polymer of a composite, as described above, and DNA may be used to aid in transfection, i.e. the uptake of DNA into an animal (e.g. human) cell. (Boussif, O. *Proceedings of the National Academy of Sciences,* 92:7297-7301 (1995); Zanta et al. *Bioconjugate Chemistry,* 8:839-844 (1997)).

The therapeutic agent is not an integral part of the multi-dimensional polymer network of the supramolecular complex. Upon encapsulation, the therapeutic agent may or may not retain its biological or therapeutic activity. Regardless, upon decomplexation or uncrosslinking of the supramolecular complex, specifically, of the multi-dimensional polymer network, the activity of the therapeutic agent is restored. Accordingly, encapsulation of the therapeutic agent affords, advantageously, protection against loss of activity due to, for example, degradation and offers enhanced bioavailability. Encapsulation of a lipophilic therapeutic agent offers enhanced, if not complete, solubility of the lipophilic therapeutic agent. The therapeutic agent may be further modified with at least one ligand prior to or after composite or supramolecular complex formation, as described above.

The therapeutic agent may be any lipophilic or hydrophilic, synthetic or naturally occurring biologically active therapeutic agent including those known in the art. Examples of suitable therapeutic agents include, but are not limited to, antibiotics, steroids, polynucleotides (e.g. genomic DNA, cDNA, mRNA and antisense oligonucleotides), plasmids, peptides, peptide fragments, small molecules (e.g. doxorubicin), chelating agents (e.g. deferoxamine (DESFERAL), ethylenediaminetetraacetic acid (EDTA)), natural products (e.g. Taxol, Amphotericin), and other biologically active macromolecules such as, for example, proteins and enzymes.

A supramolecular complex of the invention may be, for example, a solid, liquid, suspension, or emulsion. Preferably a supramolecular complex of the invention is in a form that can be injected intravenously. Other modes of administration of a supramolecular complex of the invention include, depending on the state of the supramolecular complex, methods known in the art such as, but not limited to, oral administration, topical application, parenteral, intravenous, intranasal, intraocular, intracranial or intraperitoneal injection. Prior to administration, a supramolecular complex may be isolated and purified by any means known in the art including, for example, centrifugation, dialysis and/or lyophilization.

Depending upon the type of therapeutic agent used, a supramolecular complex of the invention may be used in a variety of therapeutic methods (e.g. DNA vaccines, antibiotics, antiviral agents) for the treatment of inherited or acquired disorders such as, for example, cystic fibrosis, Gaucher's disease, muscular dystrophy, AIDS, cancers (e.g. multiple myeloma, leukemia, melanoma, and ovarian carcinoma), cardiovascular conditions (e.g., progressive heart failure, restenosis, and hemophilia), and neurological conditions (e.g., brain trauma). According to the invention, a method of treatment administers a therapeutically effective amount of a supramolecular complex as prepared by a method of the invention. A therapeutically effective amount, as recognized by those of skill in the art, will be determined on a case by case basis. Factors to be considered include, but are not limited to, the disorder to be treated and the physical characteristics of the one suffering from the disorder.

In another embodiment of the invention, the therapeutic agent is at least one biologically active compound having agricultural utility. The agriculturally biologically active compounds include those known in the art. For example, suitable agriculturally biologically active compounds include, but are not limited to, fungicides, herbicides, insecticides, and mildewcides.

The following examples are given to illustrate the invention. It should be understood, however, that the invention is not to be limited to the specific conditions or details described in these examples.

EXAMPLES

Materials. β-cyclodextrin (Cerestar USA, Inc. of Hammond, Ind.) was dried in vacuo (<0.1 mTorr) at 120° C. for 12 h before use. Biphenyl-4,4'-disulfonyl chloride (Aldrich Chemical Company, Inc. of Milwaukee, Wis.) was recrystallized from chloroform/hexanes. Potassium iodide was powdered with a mortar and pestle and dried in an oven at 200° C. All other reagents were obtained from commercial suppliers and were used as received without further purification. Polymer samples were analyzed on a Hitachi HPLC system equipped with an Anspec RI detector, a Precision Detectors DLS detector, and a Progel-TSK $G3000_{PWXL}$ column using 0.3 M NaCl or water as eluant at a 1.0 mL·min$^{-1}$ flow rate.

Example 1

Biphenyl-4,4'-disulfonyl-A,D-Capped β-Cyclodextrin, 1 (Tabushi et al. *J. Am. Chem. Soc.* 106, 5267-5270 (1984))

A 500 mL round bottom flask equipped with a magnetic stirbar, a Schlenk adapter and a septum was charged with 7.92 g (6.98 mmol) of dry β-cyclodextrin and 250 mL of anhydrous pyridine (Aldrich Chemical Company, Inc.). The resulting solution was stirred at 50° C. under nitrogen while 2.204 g (6.28 mmol) of biphenyl-4,4'-disulfonyl chloride was added in four equal portions at 15 min intervals. After stirring at 50° C. for an additional 3 h, the solvent was removed in vacuo and the residue was subjected to reversed-phase column chromatography using a gradient elution of 0-40% acetonitrile in water. Fractions were analyzed by high performance liquid chromatography (HPLC) and the appropriate fractions were combined. After removing the bulk of the acetonitrile on a rotary evaporator, the resulting aqueous suspension was lyophilized to dryness. This afforded 3.39 g (38%) of 1 as a colorless solid.

Example 2

$6^A,6^D$-Diiodo-$6^A,6^D$-Dideoxy-β-cyclodextrin, 2 (Tabushi et al. *J. Am. Chem.* 106, 4580-4584 (1984))

A 40 mL centrifuge tube equipped with a magnetic stirbar, a Schlenk adapter and a septum was charged with 1.02 g (7.2 mmol) of 1, 3.54 g (21.3 mmol) of dry, powdered potassium iodide (Aldrich) and 15 mL of anhydrous N,N-dimethylformamide (DMF) (Aldrich). The resulting suspension was stirred at 80° C. under nitrogen for 2 h. After cooling to room temperature, the solids were separated by filtration and the supernatant was collected. The solid precipitate was washed with a second portion of anhydrous DMF and the supernatants were combined and concentrated in vacuo. The residue was then dissolved in 14 mL of water and cooled in an ice bath before 0.75 mL (7.3 mmol) of tetrachloroethylene (Aldrich) was added with rapid stirring. The precipitated inclusion complex was filtered on a medium glass frit and washed with a small portion of acetone before it was dried under vacuum over $P_2O_5$ for 14 h. This afforded 0.90 g (92%) of 2 as a white solid.

Example 3

$6^A,6^D$-Diazido-$6^A,6^D$-Dideoxy-β-cyclodextrin, 3 (Tabushi et al. *Tetrahedron Lett.* 18, 1527-1530 (1977))

A 100 mL round bottom flask equipped with a magnetic stirbar, a Schlenk adapter and a septum was charged with 1.704 g (1.25 mmol) of β-cyclodextrin diiodide, 0.49 g (7.53 mmol) of sodium azide (EM Science of Gibbstown, N.J.) and 10 mL of anhydrous N,N-dimethylformamide (DMF). The resulting suspension was stirred at 60° C. under nitrogen for 14 h. The solvent was then removed in vacuo. The resulting residue was dissolved in enough water to make a 0.2 M solution in salt and then passed through 11.3 g of Biorad AG501-X8(D) resin to remove residual salts. The eluant was then lyophilized to dryness yielding 1.232 g (83%) of 3 as a white amorphous solid which was carried on to the next step without further purification.

Example 4

$6^A,6^D$-Diamino-$6^A,6^D$-Dideoxy-β-cyclodextrin, 4 (Mungall et al., *J. Org. Chem.* 1659-1662 (1975))

A 250 mL round bottom flask equipped with a magnetic stirbar and a septum was charged with 1.232 g (1.04 mmol) of β-cyclodextrin bisazide and 50 mL of anhydrous pyridine (Aldrich). To this stirring suspension was added 0.898 g (3.42 mmol) of triphenylphosphine. The resulting suspension was stirred for 1 h at ambient temperature before 10 mL, of concentrated aqueous ammonia was added. The addition of ammonia was accompanied by a rapid gas evolution and the solution became homogeneous. After 14 h, the solvent was removed in vacuo and the residue was triturated with 50 mL of water. The solids were filtered off and the filtrate was made acidic (pH<4) with 10% HCl before it was applied to an ion exchange column containing Toyopearl SP-650M ($NH_4^+$ form) resin. The product 4 was eluted with a gradient of 0-0.5 M ammonium bicarbonate. Appropriate fractions were combined and lyophilized to yield 0.832 g (71%) of the product 4 as the bis(hydrogen carbonate) salt.

Example 5

β-Cyclodextrin-DSP copolymer, 5

A 20 mL scintillation vial was charged with a solution of 92.6 mg ($7.65 \times 10^{-5}$ mol) of the bis(hydrogen carbonate) salt of 4 in 1 mL of water. The pH of the solution was adjusted to 10 with 1 M NaOH before a solution of 30.9 mg ($7.65 \times 10^{-5}$ mol) of dithiobis(succinimidyl propionate) (DSP, Pierce Chemical Co. of Rockford, Ill.) in 1 mL of chloroform was added. The resulting biphasic mixture was agitated with a Vortex mixer for 0.5 h. The aqueous layer was then decanted and extracted with 3×1 mL of fresh chloroform.

The aqueous polymer solution was then subjected to gel permeation chromatography (GPC) on Toyopearl HW-40F resin using water as eluant. Fractions were analyzed by GPC and appropriate fractions were lyophilized to yield 85 mg (85%) as a colorless amorphous powder.

Example 6

α-cyclodextrin-DSS copolymer, 6

A β-cyclodextrin-DSS copolymer, 6, was synthesized in a manner analogous to the DSP polymer, 5, except that disuccinimidyl suberate (DSS, Pierce Chemical Co. of Rockford, Ill.) was substituted for the DSP reagent. Compound 6 was obtained in 67% yield.

Example 7

β-Cyclodextrin-DTBP copolymer, 7

A 20 mL scintillation vial was charged with a solution of 91.2 mg ($7.26 \times 10^{-5}$ mol) of the bis(hydrogen carbonate) salt of 4 in 1 mL of water. The pH of the solution was adjusted to 10 with 1 M NaOH before 22.4 mg ($7.26 \times 10^{-5}$ mol) of dimethyl 3,3'-dithiobis(propionimidate).2HCl (DTBP, Pierce Chemical Co. of Rockford, Ill.) was added. The resulting homogeneous solution was agitated with a Vortex mixer for 0.5 h. The aqueous polymer solution was then subjected to gel permeation chromatography (GPC) on Toyopearl HW-40F resin. Fractions were analyzed by GPC and appropriate fractions were lyophilized to yield 67 mg (67%) of a colorless amorphous powder.

Example 8

Polyethylene glycol 600 dihydrazide, 8

A 100 mL round bottom flask equipped with a magnetic stirbar and a reflux condenser was charged with 1.82 g (3.0 mmol) of polyethylene glycol 600 (Fluka Chemical Corp of Milwaukee, Wis.), 40 mL of absolute ethanol (Quantum Chemicals Pty Ltd of Tuscola, Ill.) and a few drops of sulfuric acid. The resulting solution was heated to reflux for 14 h. Solid sodium carbonate was added to quench the reaction and the solution of the PEG diester was transferred under nitrogen to an addition funnel. This solution was then added dropwise to a solution of 0.6 mL (9.0 mmol) of hydrazine hydrate (Aldrich) in 10 mL of absolute ethanol. A small amount of a cloudy precipitate formed. The resulting solution was heated to reflux for 1 h before it was filtered and concentrated. GPC analysis revealed a higher molecular weight impurity contaminating the product. Gel permeation chromatography on Toyopearl HW-40 resin enabled a partial purification of this material to approximately 85% purity.

Example 9

Oxidation of β-cyclodextrin-DSS copolymer, 9
(Hisamatsu et al., *Starch* 44, 188-191 (1992))

The β-cyclodextrin-DSS copolymer 6 (92.8 mg, $7.3 \times 10^{-5}$ mol) was dissolved in 1.0 mL of water and cooled in an ice bath before 14.8 mg ($7.3 \times 10^{-5}$ mol) of sodium periodate was added. The solution immediately turned bright yellow and was allowed to stir in the dark at 0° C. for 14 h. The solution was then subjected to gel permeation chromatography (GPC) on Toyopearl HW-40 resin using water as eluant. Fractions were analyzed by GPC. Appropriate fractions were combined and lyophilized to dryness to yield 84.2 mg (91%) of a light brown amorphous solid.

Example 10

Polyethylene Glycol (PEG) 600 Diacid Chloride, 10

A 50 mL round bottom flask equipped with a magnetic stirbar and a reflux condenser was charged with 5.07 g (ca. 8.4 mmol) of polyethylene glycol 600 diacid (Fluka Chemical Corp of Milwaukee, Wis.) and 10 mL of anhydrous chloroform (Aldrich). To this stirring solution was added 3.9 mL (53.4 mmol) of thionyl chloride (Aldrich) and the resulting solution was heated to reflux for 1 h, during which time gas evolution was evident. The resulting solution was allowed to cool to room temperature before the solvent and excess thionyl chloride were removed in vacuo. The resulting oil was stored in a dry box and used without purification.

Example 11

β-Cyclodextrin-PEG 600 copolymer, 11

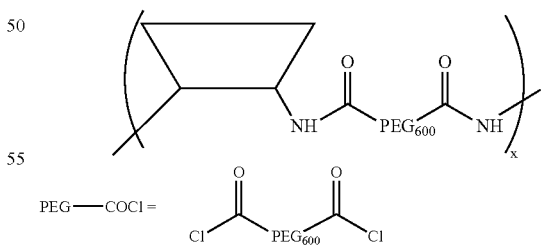

A 20 mL scintillation vial was charged with a solution of 112.5 mg ($8.95 \times 10^{-5}$ mol) of the bis(hydrogen carbonate) salt of $6^A,6^D$-diamino-$6^A,6^D$-dideoxy-β-cyclodextrin, 50 μL ($3.6 \times 10^{-4}$ mol) of triethylamine (Aldrich), and 5 mL of anhydrous N,N-dimethylacetamide (DMAc, Aldrich). The resulting suspension was then treated with 58 mg ($9.1 \times 10^{-5}$ mol) of polyethylene glycol 600 diacid chloride, 10. The resulting solution was agitated with a Vortex mixer for 5 minutes and then allowed to stand at 25° C. for 1 h during which time it became homogeneous. The solvent was removed in vacuo and the residue was subjected to gel permeation chromatography on Toyopearl HW-40F resin using water as eluant. Fractions were analyzed by GPC and appropriate fractions were lyophilized to dryness to yield 115 mg (75%) of a colorless amorphous powder.

Example 12

β-Cyclodextrin-DSP copolymer, 12

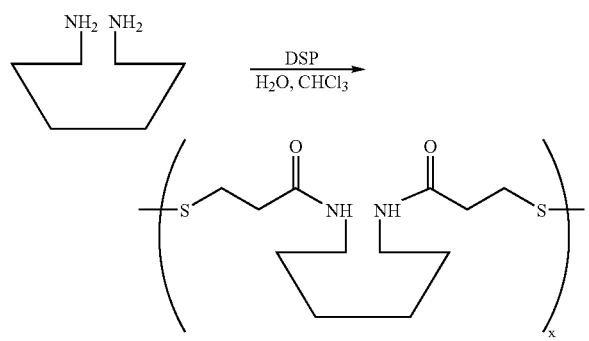

A 8 mL vial was charged with a solution of 102.3 mg (8.80×10$^{-5}$ mol) of 2$^A$,3$^A$-diamino-2$^A$,3$^A$-dideoxy-β-cyclodextrin in 1 mL of water. The pH of the solution was adjusted to 10 with 1 M NaOH before a solution of 36.4 mg (8.80×10$^{-5}$ mol) of dithiobis(succinimidyl propionate) (DSP, Pierce Chemical Co. of Rockford, Ill.) in 1 mL of chloroform was added. The resulting biphasic mixture was agitated with a Vortex mixer for 0.5 h. The aqueous layer was then decanted and extracted with 3×1 mL of fresh chloroform. The aqueous polymer solution was then subjected to gel permeation chromatography.

Example 13

6$^A$,6$^D$-Bis-(2-aminoethylthio)-6$^A$,6$^D$-dideoxy-β-cyclodextrin, 13 (Tabushi, I: Shimokawa, K; Fugita, K. *Tetrahedron Lett.* 1977, 1527-1530)

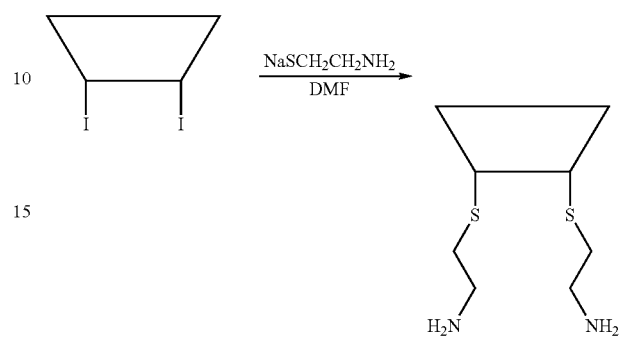

A 25 mL Schlenk flask equipped with a magnetic stirbar and a septum was charged with 0.91 mL (7.37 mmol) of a 0.81 M solution of sodium 2-aminoethylthiolate in ethanol. (Fieser, L. F.; Fiester, M. *Reagents for Organic Synthesis*; Wiley: New York, 1967; Vol. 3, pp. 265-266). The solution was evaporated to dryness and the solid was redissolved in 5 mL of anhydrous DMF (Aldrich). 6$^A$,6$^D$-Diiodo-6$^A$,6$^D$-dideoxy-β-cyclodextrin (100 mg, 7.38×10$^{-5}$ mol) was added and the resulting suspension was stirred at 60° C. under nitrogen for 2 h. After cooling to room temperature, the solution was concentrated in vacuo and the residue was redissolved in water. After acidifying with 0.1 N HCl, the solution was applied to a Toyopearl SP-650M ion-exchange column (NH$_4^+$ form) and the product was eluted with a 0 to 0.4 M ammonium bicarbonate gradient. Appropriate fractions were combined and lyophilized to dryness. This afforded 80 mg (79%) of 13 as a white powder.

Example 14

β-Cyclodextrin(cystamine)-DTBP copolymer, 14

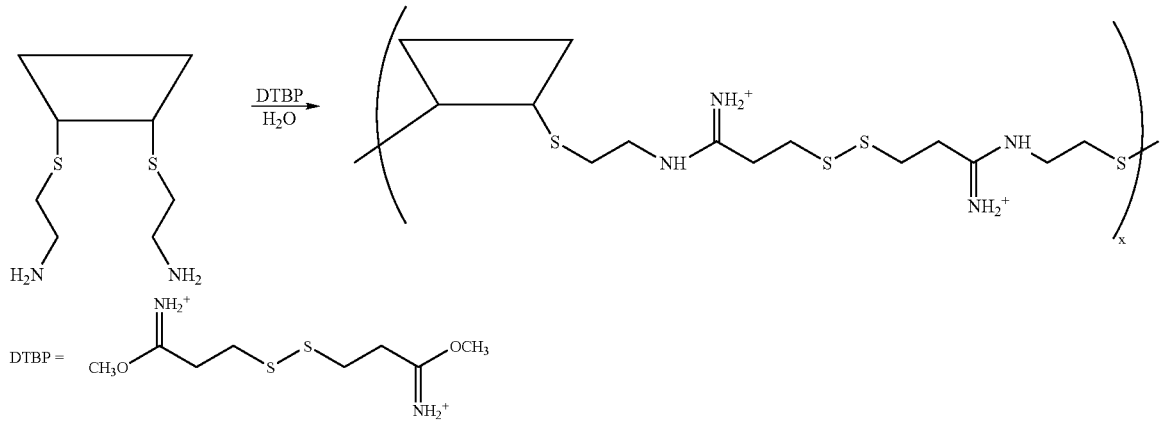

A 4 mL vial was charged with a solution of 19.6 mg (1.42×10$^{-5}$ mol) of the bis(hydrogen carbonate) salt of 13 in 0.5 mL of 0.1 M NaHCO$_3$. The solution was cooled in an ice bath before 4.4 mg (1.4×10$^{-5}$ mol) of dimethyl 3,3'-dithiobispropionimidate-2HCl (DTBP, Pierce Chemical Co. of Rockford, Ill.) was added. The resulting solution was then agitated with a Vortex mixer and allowed to stand at 0° C. for 1 h. The reaction was quenched with 1M Tris-HCl before it was acidified to pH 4 with 0.1N HCl. The aqueous polymer solution was then subjected to gel permeation chromatography on Toyopearl HW-40F resin. Fractions were analyzed by GPC and appropriate fractions were lyophilized to dryness. This afforded 21.3 mg (100%) of 14 as a white powder.

Example 15

β-Cyclodextrin(cystamine)-DMS copolymer, 15

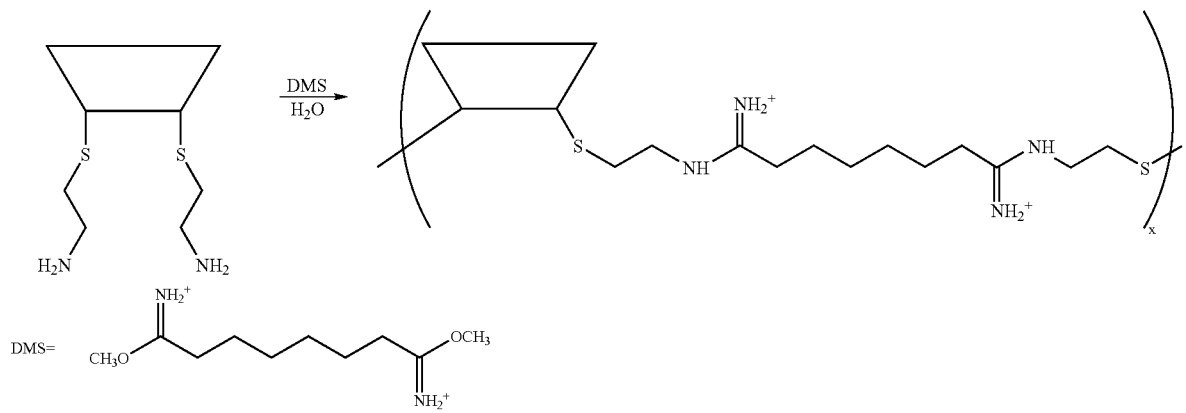

A 10 mL Schlenk flask equipped with a magnetic stirbar and a septum was charged with 200 mg ($1.60 \times 10^{-4}$ mol) of 13, 44 μL ($3.2 \times 10^{-4}$ mol) of triethylamine (Aldrich Chemical Co., Milwaukee, Wis.), 43.6 mg ($1.60 \times 10^{-4}$ mol) of dimethylsuberimidate.2HCl (DMS, Pierce Chemical Co. of Rockford, Ill.), and 3 mL of anhydrous DMF (Aldrich Chemical Co., Milwaukee, Wis.). The resulting slurry was heated to 80° C. for 18 hours under a steady stream of nitrogen during which time most of the solvent had evaporated. The residue which remained was redissolved in 10 mL of water and the resulting solution was then acidified with 10% HCl to pH 4. This solution was then passed through an Amicon Centricon Plus-20 5,000 NMWL centrifugal filter. After washing with 2×10 mL portions of water, the polymer solution was lyophilized to dryness yielding 41.4 mg (18%) of an off-white amorphous solid.

Example 16

Fixed Permanent Charged Copolymer Complexation with Plasmid

In general, equal volumes of fixed charged CD-polymer and DNA plasmid solutions in water are mixed at appropriate polymer/plasmid charge ratios. The mixture is then allowed to equilibrate and self-assemble at room temperature overnight. Complexation success is monitored by transferring a small aliquot of the mixture to 0.6% agarose gel and checking for DNA mobility. Free DNA travels under an applied voltage, whereas complexed DNA is retarded at the well.

1 μg of DNA at a concentration of 0.1 μg/μL in distilled water was mixed with 10 μL of copolymer 14 at polymer amine: DNA phosphate charge ratios of 2.4, 6, 12, 24, 36, 60, and 120. The solution was mixed manually by a micropipette and then gently mixed overnight on a lab rotator. 1 μg/μL of loading buffer (40% sucrose, 0.25% bromophenol blue, and 200 mM Tris-Acetate buffer containing 5 mM EDTA (Gao et al., *Biochemistry* 35:1027-1036 (1996)) was added to each solution the following morning. Each DNA/polymer sample was loaded on a 0.6% agarose electrophoresis gel containing 6 μg of EtBr/100 mL in 1×TAE buffer (40 mM Tris-acetate/1 mM EDTA) and 40V was applied to the gel for 1 hour. The extent of DNA/polymer complexation was indicated by DNA retardation in the gel migration pattern. The polymer (14) retarded DNA at charge ratios of 6 and above, indicating complexation under these conditions.

Example 17

Crosslinking of Copolymer-Plasmid Complex

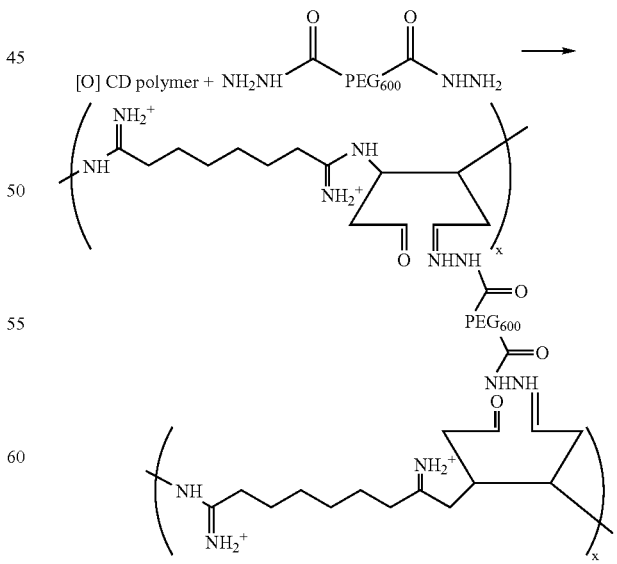

Copolymer 14 or copolymer 15 was oxidized as in Example 9. Oxidized copolymer 14 or 15 was then complexed with a DNA plasmid as in. Example 16. The solution was buffered with a borate buffer to pH 8.5 and a crosslinking agent, PEG$_{600}$-Dihydrazide, was then added and the supramolecular complex formed was analyzed by light scattering, zeta potential, and electron microscopy. Using oxidized copolymer 15, the polymer-plasmid DNA composite gave an average particle size of 90 nm by light scattering and had a surface charge of 40 mV as determined by zeta potential measurement. Upon addition of PEG$_{600}$-Dihydrazide, the supramolecular complex had an average size of 120 nm and a surface charge of 17 mV. Electron microscopy showed the composite to be uniform in size while the supramolecular complex revealed some dispersion in size.

Example 18

Transfection Studies with Plasmids Encoding Luciferase Reporter Gene

BHK-21 cells were plated in 24 well plates at a cell density of 60,000 cells/well 24 hours before transfection. Plasmids encoding the luciferase gene were mixed with the CD-polymer as in Example 16 except copolymer 14 was replaced with copolymer 15. Media solution containing the DNA/polymer complexes was added to cultured cells and replaced with fresh media after 24 hours of incubation at 37° C. The cells were lysed 48 hours after transfection. Appropriate substrates for the luciferase light assay were added to the cell lysate. Luciferase activity, measured in terms of light units produced, was quantified by a luminometer. DNA/polymer complexes successfully transfected BHK-21 cells at a charge ratios of 10, 20, 30, and 40 with maximum transfection at polymer amine:DNA phosphate charge ratio of 40. Cell lysate was also used to determine cell viability by the Lowry protein assay. (Lowry et al., *Journal of Biological Chemistry*, Vol. 193, 265-275 (1951)). No toxicity was observed up to charge ratios of 40.

Example 19

Transfection Studies with a Supramolecular Complex

The supramolecular complex formed in Example 17 was used to transfect BHK-21 cells following the procedure of Example 18. No transfection was observed.

Example 20

Crosslinking of Polyethyleneimine-Plasmid Complex

Polyethyleneimine (PEI) is complexed with a DNA plasmid as in Example 16. A crosslinking agent (for example, dimethyl 3,3'-dithiobispropionimidate (DTBP, commercially available from Pierce Chemical Co. of Rockford, Ill.); dithiobis(succinimidyl propionate) (DSP, commercially available from Pierce Chemical Co. of Rockford, Ill.) for biodegradable crosslinking; and disuccinimidyl suberate (DSS, commercially available from Pierce Chemical Co.) or dimethylsuberimidate (DMS, commercially available from Pierce Chemical Co.) for less biodegradable crosslinking) is then added and the supramolecular complex formed is analyzed by light scattering, zeta potential, and electron microscopy.

Example 21

Crosslinking Polymers Formed from DNA Template Polymerization

Template polymerization using DNA as the template is accomplished as described by Trubetskoy et al. Nucleic Acids Research, Vol. 26, No. 18, pp 4178-4185 (1998).

DNA is contacted with AEPD and comonomers A. The resultant composite of substantially linear polymer and DNA is crosslinked by adding suitable crosslinking agents (for example, DTBP, DSP, DSS, DMS) and the supramolecular complex formed is analyzed by light scattering, zeta potential, and electron microscopy.

Example 22

Crosslinking Polymers Formed from DNA Template Polymerization

Template polymerization using DNA as the template is accomplished as described by Trubetskoy et al. Nucleic Acids Research, Vol. 26, No. 18, pp 4178-4185 (1998).

DNA is contacted with oxidized cyclodextrin diamines (for example, IXa, IXb, IXc) and comonomers A. The resultant composite of substantially linear polymer and DNA is crosslinked by adding suitable crosslinking agents (for example, adipic acid dihydrazide, polyethylene glycol 600 dihydrazide 8 of Example 8) and the supramolecular complex formed is analyzed by light scattering, zeta potential, and electron microscopy.

Example 23

Thiolation of Cyclodextrin (CD) Polymer with Traut's Reagent

Under nitrogen, 10.1 mg ($7.34 \times 10^{-5}$ mol) of Traut's reagent (Pierce Chemical Co. of Rockford, Ill.) was added to 1.00 mL of a 5.0 mM solution of β-CD(cystamine)-DMS copolymer 15 in 0.1 M Na$_2$CO$_3$ (pH 10.0) containing 1.0 mM EDTA. The resulting solution was allowed to stand under nitrogen, N$_2$, at ambient temperature for 2 hours. The solution was then opened to air and filtered through an Amicon 5,000 NMWL centrifugal filter after which the supernatant was diluted with 10.0 mL of water and filtered a second time. The supernatant solution was then diluted to a 1.00 mL volume in water and stored under nitrogen. An aliquot was titrated with Ellman's reagent (Hermanson, G. T., *Bioconjugate Techniques*; Academic: New York, p. 89 (1996)) to yield a thiol content of $1.56 \times 10^{-6}$ mol, corresponding to thiol functionalization of 31% of the polymer cyclodextrin moieties.

Example 24

Air Oxidation of Thiolated Cyclodextrin (CD) Polymer

Five (5) 9 μL aliquots (total of 45 μL) of 3 mM thiolated CD polymer of Example 23 was added to 20 μL of plasmid DNA (0.24 μg/μL) at 10 minute intervals. The resulting solution was allowed to oxidize in air overnight. Electron microscopy showed the resulting supramolecular complex to be uniform in size.

Example 25

Oxidation of Thiolated Cyclodextrin (CD) Polymer with Aldrithiol

Five (5) 9 µL aliquots (total of 45 µL) of 3 mM thiolated CD polymer of Example 23 was added to 20 µL of plasmid DNA (0.24 µg/µL) at 10 minute intervals. Two equivalents of oxidizing reagent ALDRITHIOL (commercially available from Aldrich Chemical Company, Inc., Milwaukee, Wis.) based on the thiolated CD polymer was immediately added to the solution and gently mixed by pipetting. Electron microscopy showed the resulting supramolecular complex to be uniform in size.

Example 26

Synthesis of β-cyclodextrin(cystamine)-DMA copolymer, 16

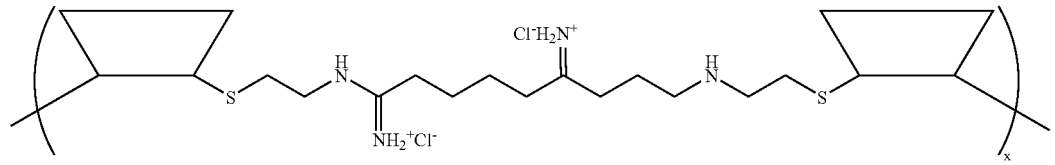

A 20 mL scintillation vial equipped with a magnetic stirbar was charged with 180 mg (0.131 mmol) of 13 and 32 mg of dimethyl adipimidate (DMA, Pierce Chemical Co. of Rockford, Ill.). To this was added 500 µl of 0.5 M $Na_2CO_3$. The resulting solution was covered with foil and stirred overnight. The mixture was acidified with 0.1 N HCl and dialyzed with Spectrapor MWCO 3,500 membrane for 2 days and lyophilized to afford 41 mg of a white amorphous solid with Mw=14 kD, as determined by light scattering.

Example 27

Synthesis of β-cyclodextrin(cystamine)-DMP copolymer, 17

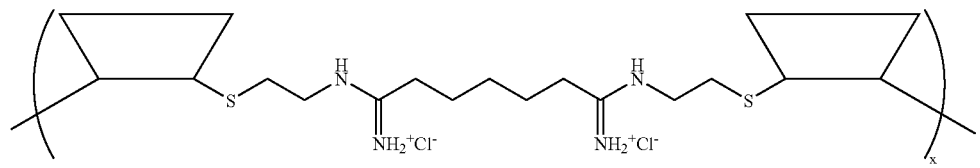

A 20 mL scintillation vial equipped with a magnetic stirbar was charged with 160 mg (0.116 mmol) of 13 and 30.1 mg of dimethyl pimelimidate (DMP, Pierce Chemical Co. of Rockford, Ill.). To this was added 500 µl of 0.5 M $Na_2CO_3$. The resulting solution was covered with foil and stirred overnight. The mixture was then acidified with 0.1 N HCl and dialyzed with Spectrapor MWCO 3,500 membrane for 2 days and lyophilized to afford 22 mg of a white amorphous solid with Mw=14 kD, as determined by light scattering.

Example 28

Transfection Studies with Plasmids Encoding Luciferase Reporter Gene

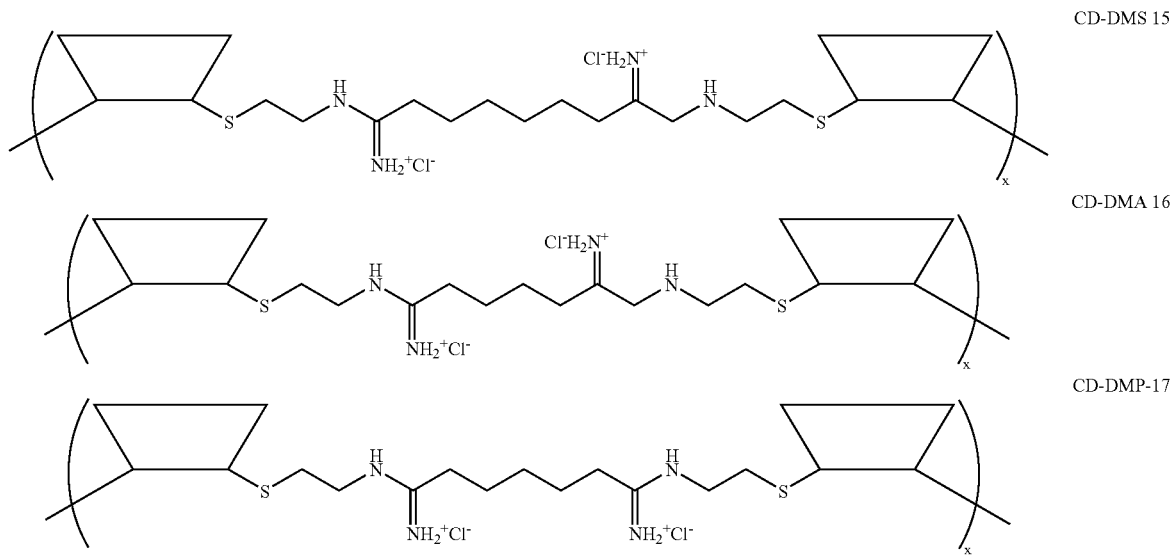

BHK-21 cells were plated in 24-well plates at cell density of 60,000 cells/well in 1 mL media. Plasmids encoding the luciferase gene were mixed with the CD-polymer as in Example 16 using copolymers 14, 15, 16, or 17. After 24 hours, media was removed and transfection mixture (200 μL of Optimem with 20 μL of polymer/DNA solution) was added to each well. After 5 hours, 800 μL of complete media (DMEM+10% BS, Gibco) was added to each well. 24 hours after transfection, media was replaced with 1 mL complete media. After another 24 hours, media was removed and cells were washed with 1 mL PBS. Cells were then lysed with 0.050 mL of Cell Culture Lysis Buffer (Promega) by one freeze-thaw cycle. 4 μL of cell lysate was used for luciferase assay, measured in terms of light units produced, and 10 μL was used for Biorad's protein DC assay. The transfection and toxicity results are illustrated in FIGS. 2A, 2B, 2C and 2D.

Example 29

Effect of Heparan Sulfate on PEI/DNA Particle

Various concentrations of linear polyethyleneimine (lPEI) 2 kD were mixed with DNA for 30 minutes. Heparan sulfate (75× of DNA) was added to the PEI/DNA solution for 30 minutes. An agarose gel was run to examine the results. At low PEI/DNA ratio, heparan sulfate was able to strip PEI away from DNA. However, at a higher concentration of PEI, PEI remained associated with the DNA even with the addition of heparan sulfate.

Example 30

Crosslinking Experiment Using Branched Polyethyleneimine (bPEI) 25 kDa with Varying Concentration of Heparan Sulfate 10 μL (1 μg) of DNA and 10 μL of polyethyleneimine (PEI, 1.41 mM, 5+/−charge ratio) was mixed together for 30 minutes. Then crosslinker dithiobispropionimidate (DTBP) or dimethylsuperimidate (DMS) was added to the DNA/PEI solution. After 90 minutes, different concentration of heparan sulfate (HS) was added for competitive binding with PEI. The agarose gel was run after 20 minutes to examine the effect of crosslinker on the binding of PEI to DNA. For 0.1−/+HS, HS could not bind to PEI to cause PEI to dissociate from DNA. Higher concentrations of HS could dissociate PEI from DNA only in the absence of DTBP (or DMS). Thus, with the presence of crosslinker on PEI, PEI has a higher affinity to DNA. However, at 3−/+HS, the concentration is high enough such that HS dissociated PEI from DNA even with the presence of crosslinker.

Example 31

Crosslinking Experiment with Pentalysine using crosslinker DTBP and reducing agent Tris(2-carboxyethyl)phosphine (TCEP)

Pentalysine was added to DNA for 15 minutes. Crosslinker DTBP was then added to the solution mixture for over 60 minutes. TCEP was added and an agarose gel was run after 30 minutes. Pentalysine itself was not strong enough to bind to the DNA. However, with the addition of crosslinker DTBP, crosslinked pentalysine bound to the DNA. When reducing agent TCEP was added, pentalysine once again dissociated from DNA. Thus, crosslinking with DTBP increased the affinity of pentalysine to DNA.

Example 32

Reversible Crosslinking of Branched PEI (bPEI) (25 kDa) with DTBP 1 ug of DNA plasmid (~5 kpb) was complexed with bPEI (25 kDa) at a 5+/−charge ratio for 30 minutes. Crosslinker DTBP (dithiobispropionimidate, Pierce Chemical Co. of Rockford, Ill.) was then added and allowed to react with the primary amines on PEI for 90 minutes. After the reaction, some of the solutions were treated with a reducing agent, TCEP (Tris2-carboxyethyl)phosphine) for 25 minutes. Heparan sulfate was then added to the mixture at a 2:1 charge ratio with respect to PEI to dissociate the particles.

Heparan sulfate was unable to dissociate crosslinked PEI from the DNA. However, after reduction of the crosslinking agent with TCEP, heparan sulfate was able to dissociate the PEI from DNA. Thus crosslinking DTBP is able to stabilize PEI/DNA composites. This stabilization is reversible under reductive conditions. The results are illustrated in the agarose gel of FIG. 1.

Example 33

β-Cyclodextrin(cystamine)-PEG600 Copolymer, 18

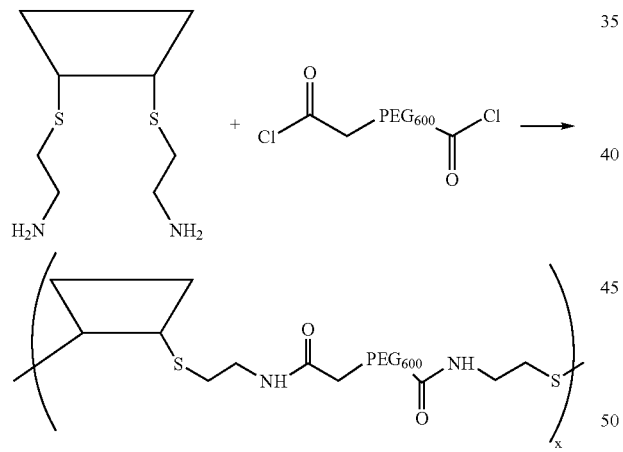

A 100 mL round-bottom flask equipped with a magnetic stirbar, a Schlenk adapter and a septum was charged with 1.564 g (1.25 mmol) of 13 and 25 mL of freshly distilled dimethylacetamide (DMAc, Aldrich). To the slurry was added 0.7 mL (4 eq) of triethylamine (Aldrich) and a solution of 10 in 5 mL of DMAc. The resulting mixture was heated to 80° C. for 2 hours. After this time, the reaction was allowed to cool to ambient temperature and the solvent was removed in vacuo. The residue was then taken up into 50 mL of water and the resulting solution dialyzed against water in a Spectra/Por 7 MWCO 3,500 membrane. The resulting solution was lyophilized to dryness to afford 1.515 g (66%) of an off-white amorphous solid with Mw=25,000, as determined by light scattering.

Example 34

Synthesis of β-Cyclodextrin-Tosylate, 19 (Melton, L. D., and Slessor, K. N., *Carbohydrate Research*, 18, p. 29 (1971))

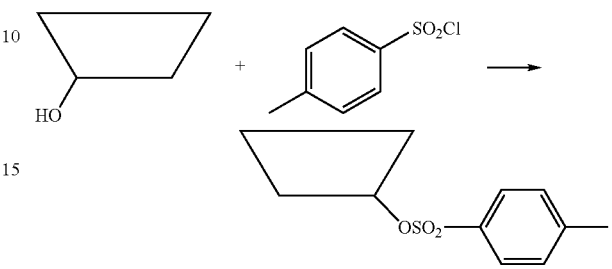

A 500 mL round-bottom flask equipped with a magnetic stirbar, a vacuum adapter and a septum was charged with a solution of dry β-cyclodextrin (8.530 g, 7.51 mmol) and 200 mL of dry pyridine. The solution was cooled to 0° C. before 1.29 g (6.76 mmol) of tosyl chloride was added. The resulting solution was allowed to warm to room temperature overnight. The pyridine was removed as much as possible in vacuo. The resulting residue was then recrystallized twice from 40 mL of hot water to yield 7.54 (88%) of a white crystalline solid.

Example 35

Synthesis of β-cyclodextrin-thiol, 20 (K. Fujita, et al., *Bioorg. Chem.*, Vol. 11, p. 72 (1982) and K. Fujita, et al., *Bioorg. Chem.*, Vol. 11, p. 108 (1982))

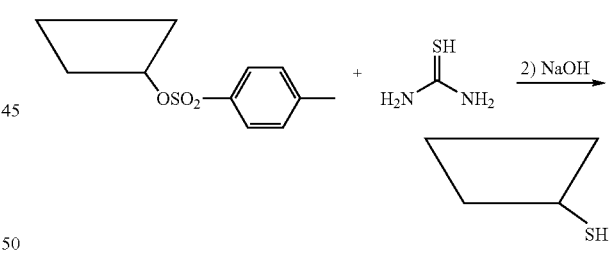

A 50 mL round bottom flask with a magnetic stirbar and a Schlenk adapter was charged with 1.00 g (0.776 mmol) of 19, 0.59 g (7.75 mmol) of thiourea (Aldrich) and 7.8 mL of 0.1N NaOH solution. The resulting mixture was heated at 80° C. for 6 hours under nitrogen. Next, 0.62 g (15.5 mmol) of sodium hydroxide was added and the reaction mixture was heated at 80° C. under nitrogen for another hour. The reaction was allowed to cool to room temperature before it was brought to pH 4.0 with 10% HCl. The total solution volume was brought to 20 mL and then was cooled in an ice bath before 0.8 mL of tetrachloroethylene was added. The reaction mixture was stirred vigorously at 0° C. for 0.5 h before the precipitated solid was collected in a fine glass frit. The solid was pumped down overnight to yield 0.60 g (67%) of a white amorphous solid.

Example 36

Synthesis of β-cyclodextrin-iodide, 21

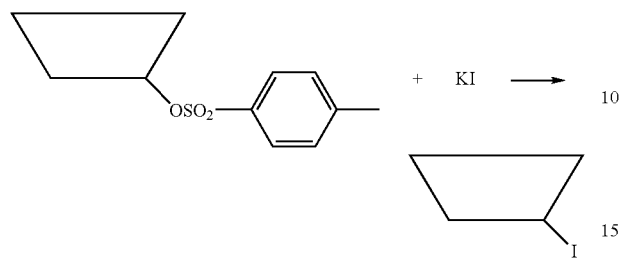

A round bottom flask with a magnetic stirbar and a Schlenk adapter is charged with 19, 15 equivalents of potassium iodide, and DMF. The resulting mixture is heated at 80° C. for 3 hours, after which the reaction is allowed to cool to room temperature. The mixture is then filtered to remove the precipitate and the filtrate evaporated to dryness and redissolved in water at 0° C. Tetrachloroethylene is added and the resulting slurry stirred vigorously at 0° C. for 20 minutes. The solid is collected on a medium glass frit, triterated with acetone and stored over $P_2O_5$.

Example 37

Synthesis of β-cyclodextrin-thiol-PEG Appended Polymer, 22

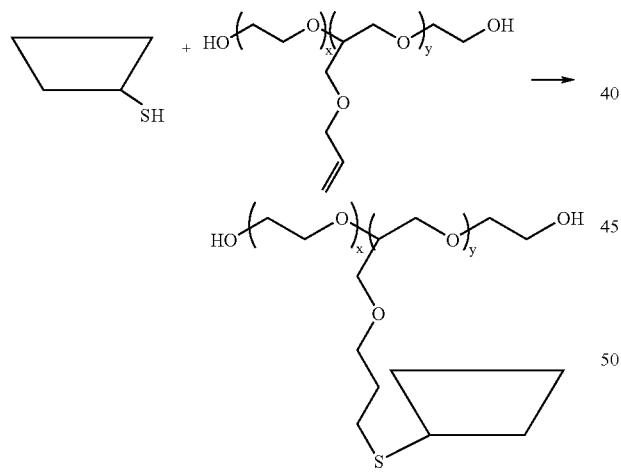

A 100 mL round-bottom flask equipped with a magnetic stirbar and a reflux condensor was charged with 2.433 g (2.11 mmol) of 20 and 0.650 g of functionalized PEG (PEG with pendant olefins, received from Yoshiyuki Koyama of Otsuma Women's University, Tokyo, Japan). The resulting mixture was heated at reflux for 12 hours, during which time 20 dissolved. The reaction mixture was allowed to cool to room temperature and precipitated solid was removed by centrifugation. The supernatant was dialyzed against water in a Spectra/Por 7 MWCO 1,000 membrane. The solution was lyophilized to give an amorphous white solid.

Example 38

Synthesis of branched PEI-cyclodextrin polymer, 23

A 20 mL scintillation vial equipped with a magnetic stirbar is charged with branched PEI (25 kD, Aldrich) and 22. To this is added degassed sodium carbonate buffer. The resulting solution stirred at 80° C. for 4 hours. The mixture is acidified with 0.1 N HCl and dialyzed with Spectra/Por MWCO 3,500 membrane for 2 days and lyophilized.

Example 39

Synthesis of hexamethylenediamine-DMS copolymer, 24

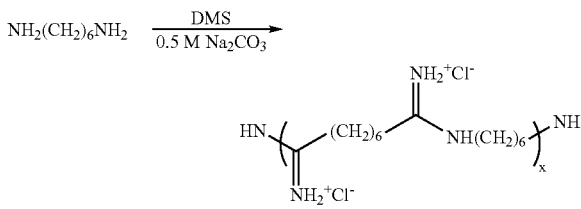

A 20 mL scintillation vial equipped with a magnetic stirbar was charged with 80 mg (0.690 mmol) of hexamethylenediamine (Aldrich) and 195 mg of dimethyl suberimidate (DMS, Pierce Chemical Co. of Rockford, Ill.). To this was added 250 µl of 0.5 M $Na_2CO_3$. The resulting solution was covered with foil and stirred overnight. The mixture was then acidified with 0.1 N HCl and dialyzed with Spectrapor MWCO 3,500 membrane for 2 days and lyophilized to afford 30 mg of a white amorphous solid.

Example 40

Synthesis of 1,9-diaminononane-DMS copolymer, 25

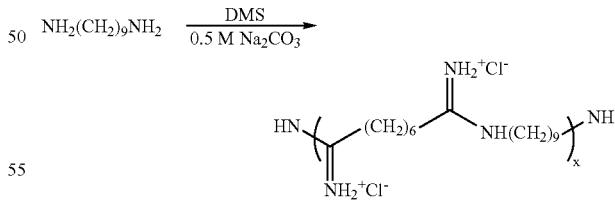

A 20 mL scintillation vial equipped with a magnetic stirbar was charged with 85 mg (0.537 mmol) of 1,9-diaminononane (Aldrich) and 146 mg of dimethyl suberimidate (DMS, Pierce Chemical Co. of Rockford, Ill.). To this was added 250 µl of 0.5 M $Na_2CO_3$. The resulting solution was covered with foil and stirred overnight. The mixture was then acidified with 0.1 N HCl and dialyzed with Spectrapor MWCO 3,500 membrane for 2 days and lyophilized to afford 41.7 mg of a white amorphous solid.

Example 41

Transfections with diamine-DMS copolymers 24 and 25

Figure 3A:
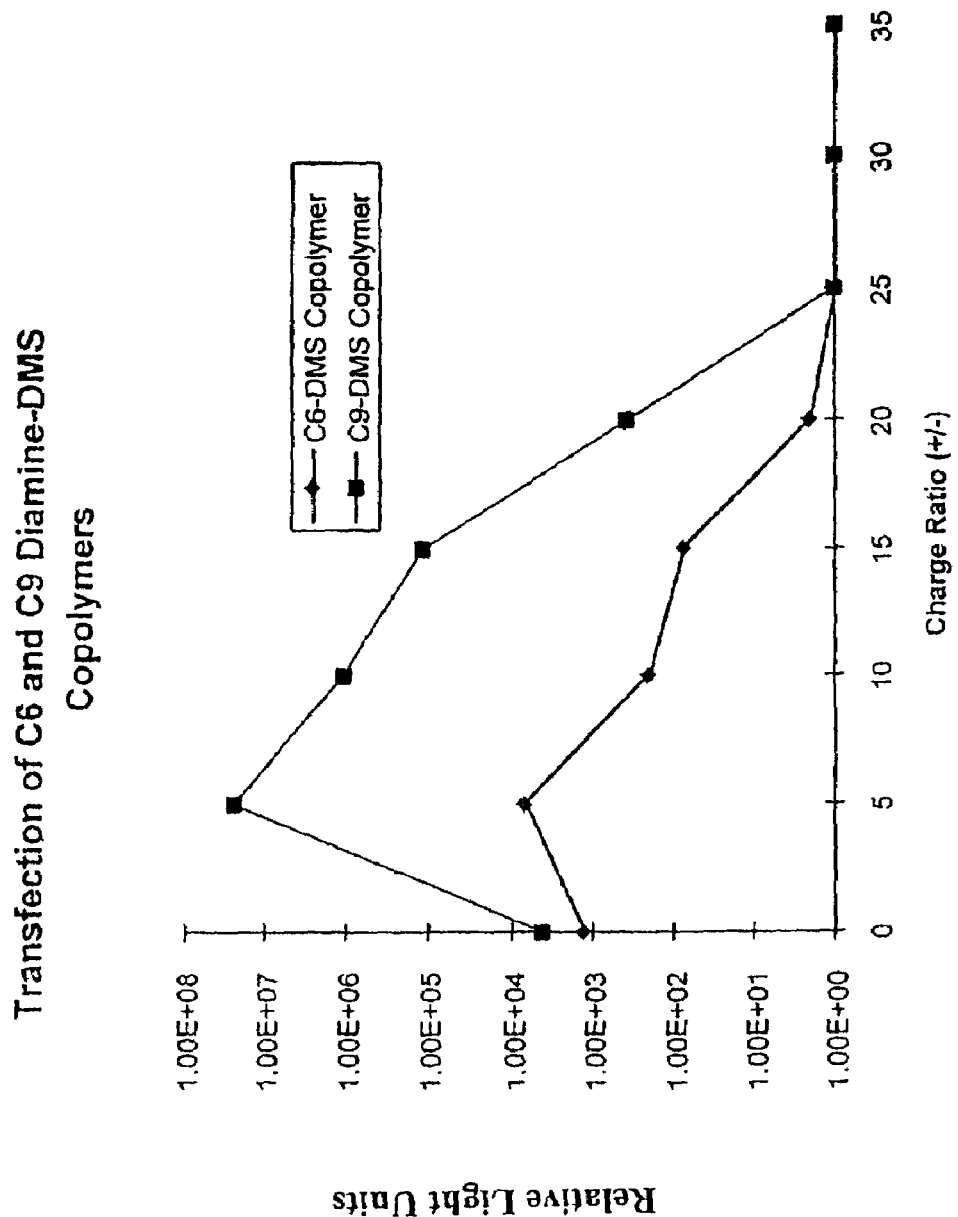
FIG. 3A. Transfection of C6 and C9 Diamine-DMS Copolymers.
Figure 3B:
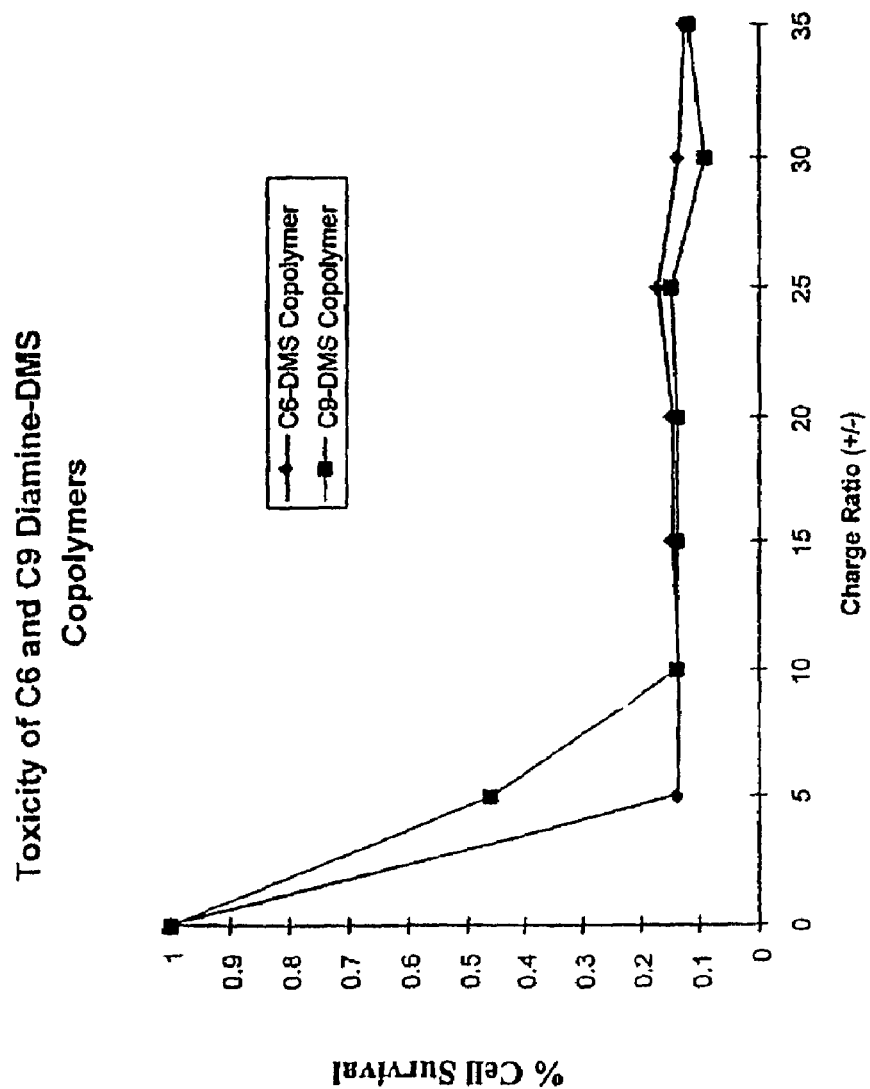
FIG. 3B. Toxicity of C6 and C9 Diamine-DMS Copolymers.

Transfections were conducted as described in Example 26, except copolymers 24 and 25 replaced copolymers 14, 15, 16, and 17. Transfection and toxicity results are illustrated in FIG. 3A and FIG. 3B, respectively. Removal of cyclodextrin from the polymer backbone results in polymers with high toxicity.

Example 42

Solubilization of Taxol with 18

Excess amounts of paclitaxel was added to an 18% solution of 18. The solutions were agitated, vortexed, and then filtered by a 2 μM nylon filter to remove any undissolved paclitaxel. The filtered solution was then injected into an HPLC equipped with an Altima C8 reverse phase column. Paclitaxel was detected by UV adsorption at 227 nm, and concentration of paclitaxel determined by peak integration. Calibration plots of paclitaxel concentration vs. peak area showed a linear relationship up to 25 μg/mL. The presence of 18% solution of 18 clearly enhanced solubility of paclitaxel greater than 30 times.

Example 43

Delivery of paclitaxel with 18 or 22

Cells are counted on a hemocytometer and plated at a density of 4,000 cells/well in 96 well plates. Paclitaxel is mixed with polymer 18 conjugated with a ligand or polymer 22 conjugated with a ligand for targeted delivery. The solutions are allowed to mix for at least 30 minutes, after which, the drug/polymer solutions are added to the cells with serial dilution. The culture plates are incubated at 37° C. After two days, the $IC_{50}$ of the paclitaxel to the cells is determined by MTT assay. The culture medium is removed, and the cells are washed with PBS. Next, 50 μL/well MTT is added, followed by 150 μL/well media. After 4 hours of incubation at 37° C., the MTT solution is removed and the formazan is solubilized by the addition of 200 μL/well DMSO. The absorbance of the formazan is read at 562 nm by a microtiter plate reader.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference in their entirety.

The invention claimed is:

1. A method of preparing a supramolecular complex comprising:
    contacting a therapeutic agent and a substantially linear cyclodextrin-containing polymer to form a composite via a covalent bond, a non-covalent bond, a non-covalent interaction, or a combination thereof; and
    covalently crosslinking said substantially linear cyclodextrin-containing polymer of said composite under conditions sufficient to form a supramolecular complex of a multi-dimensional polymer network-containing said therapeutic agent;
    wherein the cyclodextrin moieties within said substantially linear cyclodextrin-containing polymer are substituted or unsubstituted cyclodextrin moieties.

2. The method of claim 1, wherein said therapeutic agent is selected from an antibiotic, a steroid, a polynucleotide, a plasmid, a peptide, a peptide fragment, a small molecule, a chelating agent, a biologically active macromolecule, and a mixture thereof.

3. The method of claim 2, wherein said therapeutic agent is a polynucleotide.

4. The method of claim 2, wherein said therapeutic agent is a therapeutic agent comprising a ligand, whereby said ligand allows the therapeutic agent to target or bind to a cell.

5. The method of claim 4, wherein said ligand is selected from vitamins, proteins, and polysaccharides.

6. The method of claim 1, wherein said crosslinking agent is selected from adipic acid dihydrazide, polyethylene glycol 600 dihydrazide, dimethyl 3,3'-dithiobispropionimidate, dithiobis(succinimidyl propionate), disuccinimidyl suberate, and dimethylsuberimidate (DMS).

7. The method of claim 1, further comprising contacting said composite with a ligand to form a ligand-containing supramolecular complex, wherein said ligand allows said ligand-containing supramolecular complex to target or bind to a cell.

8. The method of claim 7, wherein said ligand is selected from vitamins, proteins, and polysaccharides.

9. The method of claim 1, further comprising contacting said supramolecular complex with a ligand to form a ligand-containing supramolecular complex, wherein said ligand allows said ligand-containing supramolecular complex to target or bind to a cell.

10. The method of claim 9, wherein said ligand is selected from vitamins, proteins, and polysaccharides.

11. A supramolecular complex prepared by the method of claim 1.

12. A method of delivering a therapeutic agent comprising administering, to a patient in need thereof, a therapeutically effective amount of a supramolecular complex of claim 11.

13. A supramolecular complex prepared by the method of claim 7.

14. A method of delivering a therapeutic agent comprising administering, to a patient in need thereof, a therapeutically effective amount of a supramolecular complex of claim 13.

15. A supramolecular complex prepared by the method of claim 9.

16. A method of delivering a therapeutic agent comprising administering, to a patient in need thereof, a therapeutically effective amount of a supramolecular complex of claim 15.

17. The method of claim 1, wherein said substantially linear cyclodextrin-containing polymer is a substantially linear cyclodextrin-containing copolymer having repeating units of formula Ia, Ib, or both:

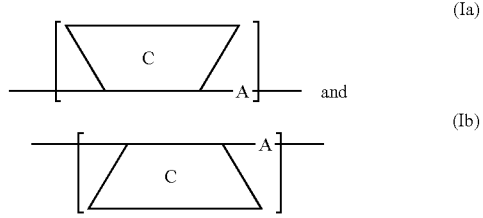

wherein C is a substituted or unsubstituted cyclodextrin monomer and A is a comonomer bound to cyclodextrin C.

18. A method of preparing a supramolecular complex comprising:
contacting a therapeutic agent and a substantially linear oxidized cyclodextrin-containing polymer to form a composite via a covalent bond, a non-covalent bond, a non-covalent interaction, or a combination thereof; and
covalently crosslinking said substantially linear oxidized cyclodextrin-containing polymer of said composite under conditions sufficient to form a supramolecular complex of a multidimensional polymer network containing said therapeutic agent;
wherein the cyclodextrin moieties within said substantially linear oxidized cyclodextrin-containing polymer are substituted or unsubstituted oxidized cyclodextrin moieties.

19. The method of claim 18, wherein said therapeutic agent is selected from an antibiotic, a steroid, a polynucleotide, a plasmid, a peptide, a peptide fragment, a small molecule, a chelating agent, a biologically active macromolecule, and a mixture thereof.

20. The method of claim 19, wherein said therapeutic agent is DNA.

21. The method of claim 18, further comprising contacting said composite or said supramolecular complex with a ligand to form a ligand-containing supramolecular complex, wherein said ligand allows the ligand-containing supramolecular complex to target or bind to a cell.

22. The method of claim 21, wherein said ligand is selected from vitamins, proteins, and polysaccharides.

23. The method of claim 18, wherein said crosslinking agent is selected from adipic acid dihydrazide, polyethylene glycol 600 dihydrazide, dimethyl 3,3'-dithiobispropionimidate, dithiobis(succinimidyl propionate), disuccinimidyl suberate, and dimethylsuberimidate (DMS).

24. A supramolecular complex prepared by a method of claim 18.

25. A method of delivering a therapeutic agent comprising administering, to a patient in need thereof, a therapeutically effective amount of a supramolecular complex of claim 24.

26. A supramolecular complex prepared by a method of claim 21.

27. A method of delivering a therapeutic agent comprising administering, to a patient in need thereof, a therapeutically effective amount of a supramolecular complex of claim 26.

28. The method of claim 18, wherein said substantially linear oxidized cyclodextrin-containing polymer is a substantially linear oxidized cyclodextrin-containing copolymer having repeating units of formula VIa, VIb, or both:

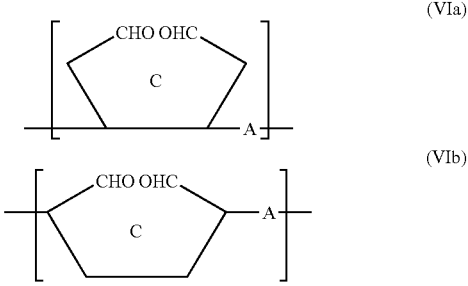

wherein C is a substituted or unsubstituted oxidized cyclodextrin monomer and A is a divalent comonomer bound to cyclodextrin C.

29. The method of claim 1, wherein said supramolecular complex is prepared in a form suitable for administration to a patient.

30. The method of claim 18, wherein said supramolecular complex is prepared in a form suitable for administration to a patient.

31. The method of claim 1, wherein the substantially linear cyclodextrin-containing polymer is crosslinked with the same species of polymer.

32. The method of claim 18, wherein the substantially linear oxidized cyclodextrin-containing polymer is crosslinked with the same species of polymer.

33. The method of claim 1, wherein the substantially linear cyclodextrin-containing polymer is crosslinked with a different species of polymer.

34. The method of claim 18, wherein the substantially linear oxidized cyclodextrin-containing polymer is crosslinked with a different species of polymer.

* * * * *